United States Patent
Desai et al.

(10) Patent No.: US 10,947,494 B2
(45) Date of Patent: Mar. 16, 2021

(54) MEDIA AND FERMENTATION METHODS FOR PRODUCING POLYSACCHARIDES IN BACTERIAL CELL CULTURE

(71) Applicant: Pfizer Inc., New York, NY (US)

(72) Inventors: Sunil Gururao Desai, Andover, MA (US); Michael Allen Hanson, Pearl River, NY (US); Jonathan Patrick Kinross, Reading, MA (US); Daniel R. Lasko, Medford, MA (US); Scott Ellis Lomberk, Suffern, NY (US); Jason Arnold Lotvin, West Nyack, NY (US); Sujata Kaushikbhai Patel-Brown, Valley Cottage, NY (US); Weiqiang Sun, Morristown, NJ (US); Peter Anthony Tomasello, Methuen, MA (US)

(73) Assignee: Pfizer Inc., New York, NY (US)

( * ) Notice: Subject to any disclaimer, the term of this patent is extended or adjusted under 35 U.S.C. 154(b) by 226 days.

(21) Appl. No.: 15/775,172

(22) PCT Filed: Nov. 10, 2016

(86) PCT No.: PCT/IB2016/056780
§ 371 (c)(1),
(2) Date: May 10, 2018

(87) PCT Pub. No.: WO2017/085602
PCT Pub. Date: May 26, 2017

(65) Prior Publication Data
US 2019/0292513 A1    Sep. 26, 2019

Related U.S. Application Data

(60) Provisional application No. 62/413,051, filed on Oct. 26, 2016, provisional application No. 62/256,347, filed on Nov. 17, 2015.

(51) Int. Cl.
*C12N 1/20* (2006.01)
*C12P 19/04* (2006.01)
*C12R 1/46* (2006.01)

(52) U.S. Cl.
CPC .............. *C12N 1/20* (2013.01); *C12P 19/04* (2013.01); *C12R 1/46* (2013.01)

(58) Field of Classification Search
None
See application file for complete search history.

(56) References Cited

U.S. PATENT DOCUMENTS

| | | | |
|---|---|---|---|
| 8,232,075 B2 | 7/2012 | Luan et al. | |
| 2010/0272755 A1* | 10/2010 | Costantino | C12P 19/04 424/244.1 |
| 2013/0252877 A1* | 9/2013 | Cai | A61K 38/011 514/1.1 |
| 2015/0052638 A1* | 2/2015 | Roemer | C12N 15/8205 800/294 |

FOREIGN PATENT DOCUMENTS

| | | |
|---|---|---|
| WO | 199854296 A1 | 12/1998 |
| WO | 2003/012058 A2 | 2/2003 |
| WO | 2007/052168 A2 | 5/2007 |
| WO | 2008011201 A2 | 1/2008 |
| WO | 2011151841 A1 | 12/2011 |
| WO | 2014/001261 A1 | 1/2014 |
| WO | 2014080423 A2 | 5/2014 |

OTHER PUBLICATIONS

Lee et al. J. Immonol. (1984) 133: 2706-2711 (Year: 1984).*
Anderson, A.S., et al., "Development of Multicomponent *Satphylococcus aureus* Vaccine Designed to Counter Multiple Bacterial Virulence Factors", Human Vaccines & Immunotherapeutics, 8(11):1585-1594 (2012).
Baker, C.J., et al., "Safety and Immunogenicity of a Bivalent Group B Streptococcal Conjugate Vaccine for Serotypes II and III", The Journal of Infectious Diseases, 188(1):66-73 (2003).
Baker, C.J., et al., "Immune Response of Healthy Women to 2 Different B Streptococcal Type V Capsular Polysaccharide-Protein Conjugate Vaccines", The Journal of Infectious Diseases, 189(6):1103-1112 (2004).
Baker, C.J., et al., "Dose-Response to Type V Group B Streptococcal Polysaccharide-Tetanus Toxoid Conjugate Vaccine in Healthy Adults", Vaccine, 25(1):55-63 (2007).
Brigtsen, A.K., et al., "Induction of Cross-Reactive Antibodies by Immunization of Healthy Adults with Types Ia and Ib Group B Streptococcal Polysaccharide-Tetanus Toxoid Conjugate Vaccines", The Journal of Infectious Diseases, 185(9):1277-1284 (2002).

(Continued)

*Primary Examiner* — Susan M Hanley
(74) *Attorney, Agent, or Firm* — Carol A. McKeever

(57) ABSTRACT

The present invention relates to media and fermentation methods for producing polysaccharides in bacterial cell culture. In one aspect, the invention relates to a complex culture medium comprising a vegetable hydrolysate, a yeast extract, and a carbon source. In another aspect, the invention relates to a defined media having a total amino acid concentration greater than about 50 mM. A further aspect of the invention relates to the use of fed batch and perfusion fermentation methods for cultivating polysaccharide-producing bacteria.

6 Claims, No Drawings

(56) References Cited

OTHER PUBLICATIONS

Ham, R.G., et al., "Clonal Growth of Mammalian Cells in a Chemically Defined, Synthetic Medium", Proc. Nat. Assoc. Sci. (USA), 53:288-293 (1965).

Marthos, B.V., et al., "Capsular Polysaccharide Production by *Streptococcus pneumoniae* Serotype 1: From Strain Selection to Fed-Batch Cultivation", Applied Microbiology Biotechnology, 99:10447-10456 (2015).

Moore, G.E., et al., "Culture of Normal Human Leukocytes" The Journal of the American Medical Association, 199(8):519-524 (1967).

Morton, H.J., "A Survey of Commercially Available Tissue Culture Media", In Vitro, 6(2):89-108 (1970).

Micoli F., et al., "Development of a glycoconjugate vaccine to prevent meningitidis in Africa caused by meningococcal serogroup X", Proc. Nat. Assoc. Sci. USA, 110(47):19077-19082 (2013).

Poutrel, B., et al., "Effects of Culture Conditions on Production of Type 5 Capsular Polysaccharide by Human and Bovine *Staphylococcus aureus* Strains", Clinical and Diagnostic Laboratory Immunology 2(2):166-171 (1995).

Smith, L.D., et al., "The growth of pasteurella pestis on a casein digest medium", Journal of the Franklin Institute 235(5):536-545 (1943).

Taylor, D., et al., "Amino acid requirements for the growth and production of some exocellular products of *Staphyloccus aureus*", Journal of Applied Bacteriology 66:319-329 (1989).

Thermofisher Scientific—Technical Resources—11595, Grace's Insect Medium, Unsupplemented [retrieved from internet on Jul. 27, 2020] <URL: https://www.thermofisher.com/au/en/home/technical-resources/media-formulation.71.html>.

Nanba et al, "Separation of the Substances from Yeast Extract to Accelerate Acetic Acid Production (Studies on the Substances to Stimulate Acetic Acid Fermentation Part VI)" Nippon Shokubin Kogyo Gakkaishi 28(10):534-541 (1981); see Table 2.

\* cited by examiner

MEDIA AND FERMENTATION METHODS FOR PRODUCING POLYSACCHARIDES IN BACTERIAL CELL CULTURE

FIELD OF THE INVENTION

The present invention relates to media and fermentation methods for producing polysaccharides in bacterial cell culture. In one aspect, the invention relates to a complex culture medium comprising a vegetable hydrolysate, a yeast extract, and a carbon source. In another aspect, the invention relates to a defined media having a total amino acid concentration greater than about 50 mM. A further aspect of the invention relates to the use of fed batch and perfusion fermentation methods for cultivating polysaccharide-producing bacteria.

BACKGROUND OF THE INVENTION

A cell surface polysaccharide refers to a polysaccharide having at least a portion located on the outermost bacterial cell membrane or bacterial cell surface, including the peptidoglycan layer, cell wall, and capsule. Cell surface polysaccharides, particularly capsular polysaccharides, have become increasingly important as therapeutic agents. Typically, a cell surface polysaccharide is associated with inducing an immune response in vivo. Some examples of polysaccharide vaccines include PNEUMOVAX® 23, which is a 23-valent vaccine for the prevention of invasive disease, such as pneumonia, febrile bacteraemia, and meningitis, caused by *Streptococcus pneumoniae*; MENCEVAX®, which is a quadrivalent vaccine for the prevention of invasive disease caused by *Neisseria meningitidis*; TYPHERIX® and TYPHIM VI®, both of which prevent typhoid fever caused by *Salmonella typhi* Vi.

Although polysaccharides are immunogenic on their own, conjugation of polysaccharides to protein carriers has been used to improve immunogenicity, particularly in infants and the elderly. The chemical bonding of the polysaccharide and protein carrier induces an immune response against bacteria displaying the polysaccharide contained within the vaccine on their surface, thus preventing disease. Accordingly, vaccination using polysaccharides from pathogenic bacteria is a potential strategy for boosting host immunity.

There are several polysaccharide-protein conjugate vaccines currently available and several more under development to address unmet therapeutic areas in need. For instance, there are three pneumococcal conjugate vaccines used to protect against invasive pneumococcal disease available on the global market: PREVNAR® (called PREVENAR™ in some countries) (heptavalent vaccine), SYNFLORIX® (a decavalent vaccine), and PREVNAR 13® (tridecavalent vaccine). MENINGITEC®, MENJUGATE®, and NEISVAC-C® are meningococcal serogroup C conjugate vaccines while MENVEO®, MENACTRA®, and NIMENRIX® are quadrivalent meningococcal conjugate vaccines that protect against *N. meningitidis* serogroups A, C, Y, and W-135. HIBERIX® prevents against disease caused by *Haemophilus influenzae* type b.

Individual monovalent polysaccharide-protein conjugates of *Streptococcus agalactiae*, also known as Group B *Streptococcus* (GBS), serotypes Ia, Ib, II, III, and V have been evaluated in phase 1 and 2 clinical trials in non-pregnant adults (Brigtsen, A. K., et al., Journal of Infectious Diseases, 185(9):1277-1284 (2002); Baker, C. J., et al., J. Infect. Dis., 188(1):66-73 (2003); Baker, C. J., et al., J. Infect. Dis., 189(6):1103-1112 (2004); Baker, C. J., et al., Vaccine, 25(1):55-63 (2007)). Bivalent II-TT and III-TT glycoconjugate vaccines and a trivalent vaccine comprising Ia-$CRM_{197}$, Ib-$CRM_{197}$ and III-$CRM_{197}$ glycoconjugates have also been studied (Baker JID 2003; Clicaltrials.gov NCT01193920, NCT01412801, and NCT01446289). However, no GBS vaccines have yet been approved.

A vaccine comprising capsular polysaccharide-protein conjugates is also being developed to prevent surgical site infections caused by *Staphylococcus aureus* (Anderson, A. S., et al., Hum. Vaccin. Immunother., 8(11):1585-1594 (2012)).

Accordingly, there is a need for the development of improved systems for producing polysaccharides by bacterial cell culture.

SUMMARY OF THE INVENTION

To meet these and other needs, the present invention relates to media and fermentation methods for producing polysaccharides in bacterial cell culture and includes the invention disclosed in U.S. Provisional Application No. 62/256,347, filed Nov. 17, 2015, the entirety of which is hereby incorporated by reference. The following clauses describe some aspects and embodiments of the invention.

One aspect of the invention relates to a polysaccharide-producing bacterial cell culture medium comprising a vegetable hydrolysate, a yeast extract, and a carbon source. In one embodiment, the vegetable hydrolysate may be a soy hydrolysate, such as HYPEP 1510 (Kerry Group Services Ltd.), HYPEP 4601 (Kerry Group Services Ltd.), HYPEP 5603 (Kerry Group Services Ltd.), HY-SOY (Kerry Group Services Ltd.), AMI-SOY (Kerry Group Services Ltd.), N-Z-SOY (Kerry Group Services Ltd.), N-Z-SOY BL4 (Kerry Group Services Ltd.), N-Z-SOY BL7 (Kerry Group Services Ltd.), SHEFTONE D (Kerry Group Services Ltd.), SE50M, SE50MK, soy peptone, BACTO Soytone (Difco Laboratories Inc.), NUTRISOY 2207 (Archer Daniels Midland Company (ADM)), NUTRISOY (ADM), NUTRISOY FLOUR (ADM), or soybean meal. In another embodiment, the concentration of the soy hydrolysate may be between about 5 g/L and about 75 g/L, such as between about 10 g/L and about 50 g/L, or about 28 g/L.

In a further embodiment, the yeast extract may be a yeast autolysate, an ultrafiltered yeast extract, or a synthetic yeast extract. In a particular embodiment, the yeast extract is an ultrafiltered yeast extract, such as AMBERFERM 5902 (Sensient Technologies Corp.), BD DIFCO (BD Biosciences), HYPEP YE (Kerry Group Services Ltd.), HY-YEST 412 (Kerry Group Services Ltd.), HY-YEST 441 (Kerry Group Services Ltd.), HY-YEST 444 (Kerry Group Services Ltd.), HY-YEST 455 (Kerry Group Services Ltd.), HY-YEST 504 (Kerry Group Services Ltd.), or ULTRAPEP YE (Kerry Group Services Ltd.). In yet another embodiment, the concentration of yeast extract is between about 1 g/L to about 50 g/L, such as between about 5 g/L to about 25 g/L, or about 10 g/L.

In one embodiment, the carbon source may be glucose, dextrose, mannitol, lactose, sucrose, fructose, galactose, raffinose, xylose, or mannose. In a particular embodiment, the carbon source is glucose. In a further embodiment, the concentration of the carbon source is between about 25 g/L to about 100 g/L, such as between about 50 g/L to about 90 g/L, or about 80 g/L.

In one embodiment, the medium further comprises a phosphate-containing ingredient, such as $Na_2HPO_4$, $K_2HPO_4$ or $KH_2PO_4$.

In another embodiment, the medium further comprises at least one amino acid, vitamin, nucleoside, or inorganic salt.

Another aspect of the invention relates to a chemically-defined polysaccharide-producing bacterial cell culture medium having a total amino acid concentration greater than about 50 mM. In one embodiment, the medium comprises a total glycine concentration of between about 1.5 mM and about 60.0 mM, such as between about 5.0 mM and about 15.0 mM, or about 7.5 mM. In another embodiment, the medium comprises a total arginine concentration of between about 1.0 mM and about 30.0 mM, such as between about 1.0 mM and about 20.0 mM, or about 4.0 mM. In a further embodiment, the medium comprises a total cysteine concentration of between about 0.1 mM and about 5.0 mM, such as between about 0.1 mM and about 3.5 mM, or about 0.4 mM. In yet another embodiment, the medium comprises a total serine concentration of between about 5.0 mM and about 75.0 mM, such as between about 5.0 mM and about 15.0 mM, or about 7.5 mM. In another embodiment, the medium comprises a total glutamine concentration of between about 1.0 mM and about 30.0 mM, such as between about 1.0 mM and about 20.0 mM, or about 4.0 mM. In a further embodiment, the medium comprises a total concentration of tyrosine of between about 0.1 mM and about 5.0 mM, such as between about 1.0 mM and about 3.5 mM, or between about 2.9 mM and about 3.0 mM. In yet another embodiment, the medium comprises a total concentration of asparagine of between about 5.0 mM and about 50.0 mM, such as between about 10.0 mM and about 30.0 mM, or about 20.0 mM. In a particular embodiment, the medium does not contain asparagine.

In one embodiment, the medium further comprises a potassium salt, such as potassium chloride or potassium sulfate. In an embodiment, the total concentration of potassium salt is between about 0.1 g/L and about 25 g/L, such as between about 0.2 g/L and about 1.25 g/L, or about 0.9 g/L.

In one embodiment, the medium further comprises a carbon source, such as glucose, dextrose, mannitol, lactose, sucrose, fructose, galactose, raffinose, xylose, or mannose. In a particular embodiment, the carbon source is glucose. In an embodiment, the total concentration of the carbon source may be between about 25 g/L and about 100 g/L, such as between about 25 g/L and about 80 g/L, or about 50 g/L.

In one embodiment, the medium further comprises sodium bicarbonate. In an embodiment, the concentration of sodium bicarbonate may be between about 0.1 g/L and about 20 g/L, such as between about 0.5 g/L and about 1.0 g/L, or about 0.84 g/L.

In one embodiment, the medium further comprises a yeast extract, such as a yeast autolysate, an ultrafiltered yeast extract, or a synthetic yeast extract. In a particular embodiment, the yeast extract is an ultrafiltered yeast extract, such as AMBERFERM 5902 (Sensient Technologies Corp.), BD DIFCO (BD Biosciences), HYPEP YE (Kerry Group Services Ltd.), HY-YEST 412 (Kerry Group Services Ltd.), HY-YEST 441 (Kerry Group Services Ltd.), HY-YEST 444 (Kerry Group Services Ltd.), HY-YEST 455 (Kerry Group Services Ltd.), HY-YEST 504 (Kerry Group Services Ltd.), or ULTRAPEP YE (Kerry Group Services Ltd.). In a further embodiment, the concentration of yeast extract is between about 1 g/L to about 50 g/L, such as between about 5 g/L to about 25 g/L, or about 10 g/L.

In a particular embodiment, the medium comprises at least about 50 mM of amino acids, a potassium salt, a carbon source, and optionally, a yeast extract.

In another embodiment, the medium comprises at least about 50 mM of amino acids, between about 5.0 mM and about 15.0 mM of glycine, between about 0.2 g/L and about 1.25 g/L of a potassium salt, between about 25 g/L and about 100 g/L of a carbon source, and between about 5 g/L to about 25 g/L of a yeast extract.

In a further embodiment, the medium comprises at least about 60 mM of amino acids, about 7.5 mM of glycine, about 0.9 g/L of potassium chloride, 50 g/L of glucose, and about 10 g/L of an ultrafiltered yeast extract.

A further aspect of the invention relates to a method of cultivating a polysaccharide-producing bacteria comprising a) adding a medium of the invention to a bioreactor, b) seeding the medium with a polysaccharide-producing bacteria, and c) cultivating the bacteria by fermentation, wherein said cultivation comprises the addition of a nutrient at a constant rate to the medium. In one embodiment, the nutrient is a carbon source, such as glucose. In one embodiment, the cultivation is carried out until the bacteria have a cell density, as determined by optical density (OD) at 600 nm, of at least 9.0. In another embodiment, the cultivated bacteria have a cell density, as determined by OD at 600 nm, of at least 9.0. In another embodiment, the cultivation is carried out until the bacteria have a polysaccharide concentration of at least about 250 mg/L. In another embodiment, the cultivated bacteria have a polysaccharide concentration of at least about 250 mg/L. In a further embodiment, the polysaccharide-producing bacteria is selected from the group consisting of *Streptococcus agalactiae, Streptococcus pneumoniae, Staphylococcus aureus, Neisseria meningitidis, Escherichia coli, Salmonella typhi, Haemophilus influenzae, Klebsiella pneumoniae, Enterococcus faecium*, and *Enterococcus faecalis*.

Yet another aspect of the invention relates to a method of cultivating a polysaccharide-producing bacteria comprising a) adding a medium as described above to a bioreactor, b) seeding the medium with a polysaccharide-producing bacteria, and c) cultivating the bacteria by perfusion, wherein the cultivation comprises (i) removing spent medium from the culture, (ii) adding fresh medium, and (iii) retaining the bacteria. In one embodiment, the rate of perfusion is between about 0.07 volumes of feed per starting culture volume per hour (VVH) to about 2.00 VVH, such as between about 0.67 VVH to about 1.33 VVH, or about 1.20 VVH. In another embodiment, the rate of perfusion is varied. For instance, in one embodiment the perfusion starts at a first rate and the rate is increased to a second rate. In another embodiment, the perfusion starts at a first rate and the rate is decreased to a second rate.

In one embodiment, the duration of perfusion is between about 1 hour and about 15 hours, such as between about 1 hour and about 10 hours, or about 7 hours.

In another embodiment, the cell growth of the cultivated bacteria is at least 2-fold greater than the cell growth in a batch fermentation system. In one embodiment, the cultivation is carried out until the bacteria have a cell density, as determined by OD at 600 nm, of at least 20.0. In a further embodiment, the cultivated bacteria have a cell density, as determined by OD at 600 nm, of at least 20.0. In yet another embodiment, the cultivation is carried out until the bacteria have a polysaccharide concentration of at least about 600 mg/L. In yet another embodiment, the cultivated bacteria have a polysaccharide concentration of at least about 600 mg/L.

In a further embodiment, the polysaccharide-producing bacteria is selected from the group consisting of *Streptococcus agalactiae, Streptococcus pneumoniae, Staphylococcus aureus, Neisseria meningitidis, Escherichia coli, Salmonella*

*typhi, Haemophilus influenzae, Klebsiella pneumoniae, Enterococcus faecium,* and *Enterococcus faecalis.*

DETAILED DESCRIPTION OF THE INVENTION

The present invention provides media and methods for producing polysaccharides by bacterial cell culture. In particular, the invention provides systems that maximize capsular polysaccharide production of encapsulated bacteria.

Before the present composition and methods are described, it is to be understood that this invention is not limited to particular methods and experimental conditions described, as such methods and conditions may vary. It is also to be understood that the terminology used herein is for purposes of describing particular embodiments only and is not intended to be limiting.

Although any methods and materials similar or equivalent to those described herein can be used in the practice or testing of the invention, the preferred methods and materials are now described. All publications mentioned herein are incorporated by reference in their entirety.

The terms used herein have the meanings recognized and known to those of skill in the art, however, for convenience and completeness, particular terms and their meanings are set forth below and throughout the specification.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

The term "about" or "approximately" means within a statistically meaningful range of a value. Such a range can be within an order of magnitude, typically within 20%, more typically still within 10%, and even more typically within 5% of a given value or range. The allowable variation encompassed by the term "about" or "approximately" depends on the particular system under study, and can be readily appreciated by one of ordinary skill in the art. Whenever a range is recited within this application, every whole number integer within the range is also contemplated as an embodiment of the invention.

The term "batch culture" as used herein refers to a method of culturing cells in which all the components that will ultimately be used in culturing the cells, including the medium as well as the cells themselves, are provided at the beginning of the culturing process. A batch culture is typically stopped at some point and the cells and/or components in the medium are harvested and optionally purified.

The term "bioreactor" as used herein refers to any vessel used for the growth of a bacterial cell culture. The bioreactor can be of any size so long as it is useful for the culturing of bacterial cells. Typically, the bioreactor will be at least 1 liter and may be 10; 50; 100; 250; 500; 1,000; 2,500; 5,000; 8,000; 10,000; 12,000 liters or more, or any volume in between. The internal conditions of the bioreactor, including, but not limited to pH and temperature, are typically controlled during the culturing period. The bioreactor can be composed of any material that is suitable for holding bacterial cell cultures suspended in media under the culture conditions of the present invention, including glass, plastic or metal. The term "production bioreactor" as used herein refers to the final bioreactor used in the production of the polysaccharide of interest. The volume of the large-scale cell culture production bioreactor is typically at least 500 liters and may be 1,000; 2,500; 5,000; 8,000; 10,000; 12,0000 liters or more, or any volume in between. One of ordinary skill in the art will be aware of and will be able to choose suitable bioreactors for use in practicing the present invention.

The term "capsular polysaccharide" or "capsule polysaccharide" refers to a glycopolymer that includes repeating units of one or more monosaccharides joined by glycosidic linkages. A capsular polysaccharide typically forms a capsule-like layer around a bacterial cell.

The term "cell density" as used herein refers to that number of cells present in a given volume of medium.

The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

Terms such as "comprises", "comprised", "comprising", "contains", "containing" and the like can have the meaning attributed to them in U.S. patent law; e.g., they can mean "includes", "included", "including" and the like. Such terms refer to the inclusion of a particular ingredients or set of ingredients without excluding any other ingredients.

The terms "consists of" and "consisting of" have the meaning ascribed to them in U.S. patent law; namely, that these terms are close-ended. Accordingly, these terms refer to the inclusion of a particular ingredient or set of ingredients and the exclusion of all other ingredients.

Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein.

The terms "culture", "cell culture" and "bacterial cell culture" as used herein refer to a bacterial cell population that is suspended in a medium under conditions suitable to survival and/or growth of the cell population. As will be clear to those of ordinary skill in the art, these terms as used herein may refer to the combination comprising the bacterial cell population and the medium in which the population is suspended.

The term "disaccharide" as used herein refers to a polysaccharide composed of two monosaccharide units or moieties linked together by a glycosidic bond.

The term "fed-batch culture" as used herein refers to a method of culturing cells in which additional components are provided to the culture at some time subsequent to the beginning of the culture process. The provided components typically comprise nutritional supplements for the cells which have been depleted during the culturing process. A fed-batch culture is typically stopped at some point and the cells and/or components in the medium are harvested and optionally purified.

These terms "medium", "cell culture medium", "bacterial culture medium", and "culture medium" as used herein refer to a solution containing nutrients which nourish growing bacterial cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "defined media"—a serum-free media that contains no proteins, hydrolysates or components of unknown composition. Defined media are free of animal-derived components and all components have a known chemical structure.

The term "metabolic waste product" as used herein refers to compounds produced by the cell culture as a result of normal or non-normal metabolic processes that are in some way detrimental to the cell culture, particularly in relation to the production of the capsular polysaccharide. For example, the metabolic waste products may be detrimental to the growth or viability of the cell culture or may decrease the amount of capsular polysaccharide produced. Exemplary metabolic waste products include lactate, which is produced as a result of glucose metabolism, and ammonium, which is produced as a result of glutamine metabolism. One goal of the present invention is to slow production of, reduce or even eliminate metabolic waste products in bacterial cell cultures.

A "monosaccharide" as used herein refers to a single sugar residue in an oligosaccharide.

An "oligosaccharide" as used herein refers to a compound containing two or more monosaccharide units or moieties. Within the context of an oligosaccharide, an individual monomer unit or moiety is a monosaccharide which is, or can be, bound through a hydroxyl group to another monosaccharide unit or moiety. Oligosaccharides can be prepared by either chemical synthesis from protected single residue sugars or by chemical degradation of biologically produced polysaccharides. Alternatively, oligosaccharides may be prepared by in vitro enzymatic methods.

The term "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium, such as metabolic waste products, are typically harvested on a continuous or semi-continuous basis and are optionally purified.

The term "polysaccharide" (PS) refers to a linear or branched polymer of at least 5 monosaccharide units or moieties. For clarity, larger number of repeating units, wherein n is greater than about 5, such as greater than about 10, will be referred to herein as a polysaccharide.

As used herein, the term "saccharide" refers to a single sugar moiety or monosaccharide unit as well as combinations of two or more single sugar moieties or monosaccharide units covalently linked to form disaccharides, oligosaccharides, and polysaccharides. The term "saccharide" may be used interchangeably with the term "carbohydrate."

The term "seeding" as used herein refers to the process of providing a cell culture to a bioreactor or another vessel. The cells may have been propagated previously in another bioreactor or vessel. Alternatively, the cells may have been frozen and thawed immediately prior to providing them to the bioreactor or vessel. The term refers to any number of cells, including a single cell.

The term "titer" as used herein refers to the total amount of polysaccharide produced by a bacterial cell culture divided by a given amount of medium volume. Titer is typically expressed in units of milligrams of polysaccharide per liter of medium.

The terms "vaccine" or "vaccine composition", which are used interchangeably, refer to pharmaceutical compositions comprising at least one immunogenic composition that induces an immune response in an animal.

Bacteria

Any bacteria having a cell wall polysaccharide may be utilized in accordance with the present invention. In a preferred embodiment, the bacteria are encapsulated bacteria. Non-limiting examples of encapsulated bacteria that may be used in accordance with the present invention include Streptococcus species, such as S. agalactiae and S. pneumoniae, Staphylococcus aureus, Neisseria meningitidis, Escherichia coli, Salmonella typhi, Haemophilus influenzae, Klebsiella pneumoniae, Enterococcus faecium, and Enterococcus faecalis. In a more preferred embodiment, the bacteria have fastidious growth requirements. Fastidious bacteria include, but are not limited to, Streptococcus species (e.g. S. agalactiae and S. pneumoniae).

There are ten different serotypes of S. agalactiae, also known as Group B Streptococcus (GBS), any of which may be used in the present invention. Those serotypes include Ia, Ib, II, III, IV, V, VI, VII, VIII, and IX. All GBS capsular polysaccharides have a branched repeat structure with a terminal $\alpha$2-3-linked sialic acid that is required for bacterial virulence. Some examples of GBS strains contemplated for use in the present invention include, but are not limited to, 090, A909 (ATCC Accession No. BAA-1138), 515 (ATCC Accession No. BAA-1177), B523, CJB524, MB 4052 (ATCC Accession No. 31574), H36B (ATCC Accession No. 12401), S40, S42, MB 4053 (ATCC Accession No. 31575), M709, 133, 7357, PFEGBST0267, MB 4055 (ATCC Accession No. 31576), 18RS21 (ATCC Accession No. BAA-1175), S16, S20, V8 (ATCC Accession No. 12973), DK21, DK23, UAB, 5401, PFEGBST0708, MB 4082 (ATCC Accession No. 31577), M132, 110, M781 (ATCC Accession No. BAA-22), D136C(3) (ATCC Accession No. 12403), M782, S23, 120, MB 4316 (M-732; ATCC Accession No. 31475), M132, K79, COH1 (ATCC Accession No. BAA-1176), PFEGBST0563, 3139 (ATCC Accession No. 49446), CZ-NI-016, PFEGBST0961, 1169-NT1, CJB111 (ATCC Accession No. BAA-23), CJB112, 2603 V/R (ATCC Accession No. BAA-611), NCTC 10/81, CJ11, PFEGBST0837, 118754, 114852, 114862, 114866, 118775, B 4589, B 4645, SS1214, CZ-PW-119, 7271, CZ-PW-045, JM9130013, JM9130672, IT-NI-016, IT-PW-62, and IT-PW-64.

There are more than 90 different serotypes of S. pneumoniae, any of which are contemplated for use in the present invention. Examples include, but are not limited to, serotypes 1, 2, 3, 4, 5, 6A, 6B, 7A, 7C, 7F, 8, 9N, 9L, 9V, 10A, 10B, 11A, 11F, 12A, 12F, 14, 15A, 15B, 15C, 17A, 17F, 18C, 19A, 19F, 20, 22F, 23A, 23B, 23F, 24F, 33F 35, 38, 39, 40, and 42. For example in one embodiment, S. pneumoniae serotypes 8, 10A, 11A, 12F, 15B, 22F or 33F may be used in the present invention. In another embodiment, S. pneumoniae serotypes 1, 3, 4, 5, 6A, 6B, 7F, 9V, 14, 18C, 19A, 19F and 23F may be used in the present invention.

Similarly, any encapsulated strain of S. aureus may be used in the present invention. Preferably, S. aureus strains producing serotype 5 or 8 capsular polysaccharides, such as Reynolds, Becker, Newman, PS80, JL278, and JL812, are contemplated.

Any strain of N. meningitidis serogroups A, C, Y, and W-135 may be used in the present invention.

Any strain of E. coli may be used in the present invention.

Any strain of *S. typhi* Vi may be used in the present invention.

Any strain of *H. influenzae* type b may be used in the present invention.

Any strain of *K. pneumoniae* may be used in the present invention.

*E. faecalis* may be used in the present invention.

Exemplary strains of *E. faecium* that may be used in the present invention include those listed in Table 1.

TABLE 1

| Strains of *E. faecium* Strain |
|---|
| E1162 (Genome GenBank accession number ABQJ00000000) |
| E0510 |
| E1760 |
| E1679 (Genome GenBank accession number ABSC00000000) |
| E1644 |
| E1716 |
| E1717 |
| E1441 |
| E1435 |
| E0734 |
| E1652 |
| E0745 |
| E0470 |
| E1340 |
| E0013 |
| E0300 |
| E0155 |
| E0161 |
| E1132 |
| E1263 |
| E1250 |
| E1283 |
| E1284 |
| E1734 |
| E1467 |
| E1500 |
| E1737 |
| E1463 |
| E1499 |
| E1735 |
| E0380 |
| E1391 |
| E1403 |
| E1421 |
| E1423 |
| E0333 |
| E1292 |
| E1620 |
| E1621 |
| E1623 |
| E1625 |
| E1636 (Genome GenBank accession number ABRY00000000) |
| E0073 |
| E0125 |
| E0772 |
| E1172 |
| E1302 |
| E1307 |
| E1308 |
| E1721 |
| U0317 (Genome GenBank accession number ABSW00000000) |
| E1728 |
| E1731 |
| E1794 (DO strain; TX0016 strain) (Genome GenBank accession number ACIY00000000) |
| E1360 |
| E1674 |
| E1675 |
| E1643 |
| E1850 |
| E0005 |
| E0321 |
| E0322 |
| E0027 |
| E1149 |

TABLE 1-continued

| Strains of *E. faecium* Strain |
|---|
| E1147 |
| E0802 |
| E0849 |
| E1316 |
| E1554 |
| E1133 |
| E1764 |
| E1766 |
| E1485 |
| E1590 |
| E0060 |
| E0128 |
| E0135 |
| E1002 |
| E1039 (Genome GenBank accession number ACOS00000000) |
| E0980 (Genome GenBank accession number ABQA00000000) |
| E1071 (Genome GenBank accession number ABQI00000000) |
| E1759 |
| E1628 |
| E1630 |
| E1573 |
| E0172 |
| E0211 |
| E0466 |
| E1574 |
| E0463 |
| E1607 |
| E1619 |
| E1576 |
| E1781 |
| E0685 |
| E0144 |
| E0045 |
| E0429 |
| E1622 |

Additionally, any number of commercially and non-commercially available bacteria having cell wall polysaccharides may be utilized in accordance with the present invention. One skilled in the art will appreciate that some bacteria have different nutrition requirements and/or might require different culture conditions for optimal growth and will be able to modify conditions as needed.

In many instances, the strains of bacteria will be selected or engineered to produce high levels of polysaccharide. In some embodiments, the bacterial cells are genetically engineered to produce high levels of polysaccharide.

Cell Culture Media

The present invention provides a variety of media formulations that maximize polysaccharide production in bacterial cell cultures.

Complex Media

Bacterial cell cultures, particularly for fastidious bacteria and/or those bacteria producing cell wall polysaccharides, are often grown in complex media such as Columbia broth, Luria-Bertani (LB) broth, Todd-Hewitt broth, GC medium, blood broth, or brain-heart infusion broth. Accordingly, a complex media was developed to maximize bacterial growth and polysaccharide production. In one aspect, the invention relates to a complex culture medium comprising a vegetable hydrolysate, a yeast extract, and a carbon source.

Suitable vegetable hydrolysates include, but are not limited to, HYPEP 1510 (Kerry Group Services Ltd.), HYPEP 4601 (Kerry Group Services Ltd.), HYPEP 5603 (Kerry Group Services Ltd.), HY-SOY (Kerry Group Services Ltd.), AMI-SOY (Kerry Group Services Ltd.), N-Z-SOY (Quest), N-Z-SOY BL4 (Kerry Group Services Ltd.), N-Z-SOY BL7 (Quest), SHEFTONE D (Kerry Group Services Ltd.), SE50M, SE50MK, soy peptone, BACTO soytone (Difco Laboratories Inc.), NUTRISOY 2207 (ADM), NUTRISOY (ADM), NUTRISOY flour (ADM), and soybean meal. In a preferred embodiment, the vegetable hydrolysate is soy hydrolysate. Preferably, the soy hydrolysate is HYPEP 1510 (Kerry Group Services Ltd.).

Concentrations of the vegetable hydrolysate in the culture medium can range between about 5 g/L and about 75 g/L, such as between about 5 g/L and about 65 g/L, between about 5 g/L and about 55 g/L, between about 5 g/L and about 45 g/L, between about 5 g/L and about 35 g/L, between about 10 g/L and about 70 g/L, between about 10 g/L and about 60 g/L, between about 10 g/L and about 50 g/L, between about 10 g/L and about 40 g/L, between about 15 g/L and about 75 g/L, between about 15 g/L and about 65 g/L, between about 15 g/L and about 55 g/L, between about 15 g/L and about 45 g/L, between about 20 g/L and about 70 g/L, between about 20 g/L and about 60 g/L, or between about 20 g/L and about 50 g/L. In a preferred embodiment, the concentration of vegetable hydrolysate in the culture medium is between about 10 g/L and about 50 g/L, most preferably about 28 g/L.

Yeast extracts suitable for use in the present invention may include yeast autolysate, ultrafiltered yeast extracts, and synthetic yeast extracts. In one aspect, the yeast extract is BD BBL (BD Biosciences), BD BACTO (BD Biosciences), HY YEST 412 (Kerry Group Services Ltd.), HY YEST 444 (Kerry Group Services Ltd.), HY-YEST 441 (Kerry Group Services Ltd.), HY-YEST 455 (Kerry Group Services Ltd.), or HY YEST 504 (Kerry Group Services Ltd.). In another aspect, the yeast extract is an ultrafiltered yeast extract, such as AMBERFERM 5902 (Sensient Technologies Corp.), BD DIFCO (BD Biosciences), HYPEP YE (Kerry Group Services Ltd.), or ULTRAPEP YE (Kerry Group Services Ltd.). In a further aspect, the yeast extract is a synthetic yeast extract, such as BD RECHARGE (BD Biosciences). Most preferably, the yeast extract is an ultrafiltered yeast extract, such as AMBERFERM 5902 (Sensient Technologies Corp.).

Concentrations of the yeast extract in the culture medium can range from about 1 g/L to about 50 g/L, such as between about 1 g/L and about 40 g/L, between about 1 g/L and about 30 g/L, between about 1 g/L and about 25 g/L, between about 1 g/L and about 20 g/L, between about 1 g/L and about 15 g/L, between about 1 g/L and about 10 g/L, between about 5 g/L and about 50 g/L, between about 5 g/L and about 40 g/L, between about 5 g/L and about 30 g/L, between about 5 g/L and about 25 g/L, between about 5 g/L and about 20 g/L, between about 5 g/L and about 15 g/L, between about 10 g/L and about 50 g/L, between about 10 g/L and about 40 g/L, between about 10 g/L and about 30 g/L, between about 10 g/L and about 35 g/L, between about 10 g/L and about 30 g/L, between about 10 g/L and about 25 g/L, between about 10 g/L and about 20 g/L, between about 15 g/L and about 50 g/L, between about 15 g/L and about 40 g/L, between about 15 g/L and about 30 g/L, or between about 15 g/L and about 25 g/L. In a preferred embodiment, the concentration of yeast extract in the culture medium is between about 5 g/L to about 25 g/L, most preferably about 10 g/L.

Any carbon source may be used in the culture medium of the present invention. Suitable carbon sources include glucose, dextrose, mannitol, lactose, sucrose, fructose, galactose, raffinose, xylose, and/or mannose. Preferably, the carbon source in the culture medium is glucose.

Concentrations of the carbon source in the culture medium can range from about 25 g/L to about 100 g/L, such as between about 25 g/L and about 90 g/L, between about 25 g/L and about 80 g/L, between about 25 g/L and about 70 g/L, between about 25 g/L and about 60 g/L, between about 25 g/L and about 50 g/L, between about 50 g/L and about 100 g/L, between about 50 g/L and about 90 g/L, between about 50 g/L and about 80 g/L, between about 50 g/L and about 70 g/L, between about 60 g/L and about 100 g/L, between about 60 g/L and about 90 g/L, between about 60 g/L and about 80 g/L, between about 70 g/L and about 100 g/L, or between about 70 g/L and about 90 g/L. In a preferred embodiment, the concentration of the carbon source in the culture medium is between about 50 g/L to about 90 g/L, most preferably about 80 g/L.

Accordingly, the inventors discovered that a combination of a vegetable hydrolysate, a yeast extract, and a carbon source helps to support maximal bacterial cell growth and polysaccharide production. In one aspect, the invention relates to a culture medium including a vegetable hydrolysate, a yeast extract, and a carbon source. The vegetable hydrolysate can be any suitable vegetable hydrolysate known in the art, such as those described above. Preferably, the hydrolysate is soy hydrolysate. More preferably, the soy hydrolysate is HYPEP 1510 (Kerry Group Services Ltd.). Any yeast extract known in the art, such as those described above, may be used. In a preferred embodiment, the yeast extract is AMBERFERM 5902 (Sensient Technologies Corp.).

In one aspect, the complex culture medium of the present invention may include phosphate-containing ingredients such as $Na_2HPO_4$, $K_2HPO_4$, or $KH_2PO_4$.

In another aspect, the culture media may include various other factors known in the art to enhance growth, such as amino acids, vitamins, nucleosides, and inorganic salts.

In yet another aspect, the cultivation is carried out using any of the methods disclosed herein until the cell density, as determined by optical density (OD) at 600 nm, of the bacterial cell culture using the complex media of the invention is at least 15.0, such as at least 16.0, 17.0, 18.0, 19.0, 20.0, 21.0, 22.0, 23.0, 24.0, 25.0, 26.0, 27.0, 28.0, 29.0 or 30.0. In a preferred embodiment, the cultivation is carried out until the cell density is at least 15.0. In yet another aspect, the cell density, as determined by optical density (OD) at 600 nm, of the bacterial cell culture using the complex media of the invention may be at least 15.0, such as at least 16.0, 17.0, 18.0, 19.0, 20.0, 21.0, 22.0, 23.0, 24.0, 25.0, 26.0, 27.0, 28.0, 29.0 or 30.0. In a preferred embodiment, the cell density is at least 15.0.

GBS polysaccharide yield may be determined by measuring sialic acid concentration. Sialic acid is released from cell bound polysaccharide by digesting pelleted cells by methods well-known in the art. The digest can be assayed by anion exchange chromatography (AEX) via high performance liquid chromatography (HPLC). Polysaccharide concentration is then determined by multiplying the sialic acid value times a repeat unit weight conversion factor. For example, the conversion factor for each GBS serotype is as follows: Ia, Ib, and III=3.24; II and V=4.29; and IV=3.77. Polysaccharide quantification for *S. pneumoniae* or other encapsulated bacteria is achieved by first releasing the capsular polysaccharide from the cell wall by treatment with a detergent, such as sodium deoxycholic acid (DOC) or sodium N-lauryl-sarcosine (NLS); acid treatment at high temperature; base treatment; and/or mechanical lysis. The released polysaccharide in the crude lysate is then assayed against an authentic standard using size exclusion chromatography (SEC) HPLC.

In one aspect, the cultivation is carried out using any of the methods disclosed herein until the polysaccharide concentration, as determined by sialic acid concentration, of the bacterial cell culture using the complex media of the invention is at least about 200 mg/L, such as at least about 250 mg/L; 300 mg/L; 350 mg/L; 400 mg/L; 450 mg/L; 500 mg/L; 550 mg/L; 600 mg/L; 650 mg/L; or 700 mg/L. In a preferred embodiment, the cultivation is carried out until the polysaccharide concentration is at least about 600 mg/L. In one aspect, the polysaccharide concentration, as determined by sialic acid concentration, of the bacterial cell culture using the complex media of the invention may be at least about 200 mg/L, such as at least about 250 mg/L; 300 mg/L; 350 mg/L; 400 mg/L; 450 mg/L; 500 mg/L; 550 mg/L; 600 mg/L; 650 mg/L; or 700 mg/L. In a preferred embodiment, the polysaccharide concentration is at least about 600 mg/L.

Defined Media

In view of the potential inconsistency of complex media, however, a chemically defined media was also investigated to maximize bacterial growth and polysaccharide production. It was surprisingly discovered that Applicant's proprietary mammalian cell culture media disclosed in U.S. Pat. No. 7,294,484, which is incorporated by reference herein in its entirety, provided both unexpectedly high cell growth and polysaccharide production. Specifically, the present inventors found that a defined media having a total amino acid concentration greater than about 50 mM provided both unexpectedly high cell growth and polysaccharide production. An exemplary mammalian cell culture media is shown in Table 2 below. Traditional media formulations begin with a relatively low level of total amino acids in comparison with the media formulations of the present invention. For example, the traditional cell culture medium known as DME-F12 (a 50:50 mixture of Dulbecco's Modified Eagle's medium and Ham's F12 medium) has a total amino acid content of 7.29 mM, and the traditional cell culture medium known as RPMI-1640 has a total amino acid content of 6.44 mM (See e.g., H. J. Morton, In Vitro, 6:89-108 (1970), R. G. Ham, Proc. Nat. Assoc. Sci. (USA), 53:288-293 (1965), G. E. Moore et al., J. Am. Medical Assn., 199:519-24 (1967), all incorporated herein by reference).

TABLE 2

Exemplary Mammalian Cell Culture Media

| Amino Acids | mg/L | mM |
| --- | --- | --- |
| alanine | 17.80 | 0.20 |
| arginine | 696.00 | 4.00 |
| asparagine•$H_2O$ | 3000.00 | 20.00 |
| aspartic acid | 219.45 | 1.65 |
| cysteine•HCl•$H_2O$ | 70.40 | 0.40 |
| cysteine•2HCl | 468.75 | 1.50 |
| monosodium glutamate | 33.80 | 0.20 |
| glutamine | 584.00 | 4.00 |
| glycine | 115.50 | 1.54 |
| histidine•HCl•$H_2O$ | 474.60 | 2.26 |
| isoleucine | 570.73 | 4.36 |
| leucine | 1030.70 | 7.87 |
| lysine•HCl | 1401.40 | 7.70 |
| methionine | 387.40 | 2.60 |
| phenylalanine | 507.00 | 3.07 |
| proline | 539.50 | 4.69 |
| serine | 1052.00 | 10.02 |
| threonine | 564.80 | 4.75 |
| tryptophan | 274.16 | 1.34 |
| tyrosine•2Na•$2H_2O$ | 745.75 | 2.86 |
| valine | 749.00 | 6.40 |

| Vitamins | mg/L | mM |
| --- | --- | --- |
| biotin | 2.68 | 0.01 |
| calcium pantothenate | 21.92 | 0.05 |
| choline chloride | 158.46 | 1.14 |

TABLE 2-continued

Exemplary Mammalian Cell Culture Media

| | | |
| --- | --- | --- |
| folic acid | 25.93 | 0.06 |
| inositol | 163.98 | 0.91 |
| nicotinamide | 26.23 | 0.22 |
| pyridoxal•HCl | 2.03 | 0.01 |
| pyridoxine•HCl | 36.13 | 0.18 |
| riboflavin | 2.41 | 0.01 |
| thiamine•HCl | 39.43 | 0.12 |
| vitamin B12 | 21.17 | 0.02 |

| Inorganic Salts | mg/L | mM |
| --- | --- | --- |
| $CaCl_2$ | 116.55 | 1.05 |
| KCl | 312.90 | 4.19 |
| $Na_2HPO_4$ | 56.60 | 0.40 |
| NaCl | 1100.00 | 18.80 |
| $NaH_2PO_4$•$H_2O$ | 645.84 | 4.68 |
| $MgSO_4$ | 138.00 | 1.15 |
| $MgCl_2$ | 28.50 | 0.30 |
| $NaHCO_3$ | 2000.00 | 23.81 |

| Trace Elements | µg/L | nM |
| --- | --- | --- |
| Sodium Selenite | 69.16 | 400.00 |
| $Fe(NO_3)_3$•$9H_2O$ | 50.00 | 123.76 |
| $CuSO_4$ | 10.24 | 64.00 |
| $CuSO_4$•$5H_2O$ | 99.88 | 400.00 |
| $FeSO_4$•$7H_2O$ | 4170 | 15000 |
| $ZnSO_4$•$7H_2O$ | 2640 | 9200 |
| $MnSO_4$•$H_2O$ | 33.80 | 200.00 |
| $Na_2SiO_3$•$9H_2O$ | 284.07 | 1000 |
| $(NH_4)_6Mo_7O_{24}$•$4H_2O$ | 247.20 | 200.00 |
| $NH_4VO_3$ | 2.34 | 20.00 |
| $NiSO_4$•$6H_2O$ | 5.26 | 20.00 |
| $SnCl_2$•$2H_2O$ | 0.90 | 4.00 |
| $AlCl_3$•$6H_2O$ | 0.97 | 4.00 |
| KBr | 0.48 | 4.00 |
| $CrCl_3$ | 15.83 | 100.00 |
| NaF | 0.17 | 4.00 |
| $GeO_2$ | 0.42 | 4.00 |
| KI | 33.20 | 200.00 |
| RbCl | 0.48 | 4.00 |
| $H_3BO_3$ | 12.37 | 200.00 |
| LiCl | 0.17 | 4.00 |

| Other Components | µg/L | nM |
| --- | --- | --- |
| Hydrocortisone | 540.00 | 1.49 |
| Putrescine•2HCl | 15000 | 93.11 |
| linoleic acid | 290.00 | 1.04 |
| thioctic acid | 716.00 | 3.48 |

| Other Components | mg/L | mM |
| --- | --- | --- |
| D-glucose (Dextrose) | 15000.00 | 83.33 |
| PVA | 2560.00 | |
| Nucellin ™ | 50.00 | |
| Sodium Pyruvate | 55.00 | 0.50 |

Accordingly, the present invention relates to a cell culture media having a total amino acid concentration of at least about 50 mM, such as at least about 55 mM, at least 60 mM, at least 70 mM, and at least 75 mM. In a preferred embodiment, the total amino acid concentration is at least 60 mM.

In an aspect of the invention, the total glycine concentration in the bacterial cell culture media can range between about 1.5 mM and about 60.0 mM, such as between about 1.5 mM and about 50.0 mM, between about 1.5 mM and about 40.0 mM, between about 1.5 mM and about 30.0 mM, between about 1.5 mM and about 20.0 mM, between about 1.5 mM and about 15.0 mM, between about 1.5 mM and about 10.0 mM, between about 1.5 mM and about 7.5 mM, between about 1.5 mM and about 5.0 mM, between about 5.0 mM and about 60.0 mM, between about 5.0 mM and about 50.0 mM, between about 5.0 mM and about 40.0 mM, between about 5.0 mM and about 30.0 mM, between about 5.0 mM and about 20.0 mM, between about 5.0 mM and about 15.0 mM, between about 5.0 mM and about 10.0 mM, between about 5.0 mM and about 7.5 mM, between about 7.5 mM and 60.0 mM, between about 7.5 mM and about 50.0 mM, between about 7.5 mM and about 40.0 mM, between about 7.5 mM and about 30.0 mM, between about 7.5 mM and about 20.0 mM, between about 7.5 mM and about 15.0 mM, or between about 7.5 mM and about 10.0 mM. In a preferred embodiment, the total concentration of glycine in the bacterial cell culture media is between about 5.0 mM and about 15.0 mM, most preferably about 7.5 mM.

In an aspect of the invention, the total arginine concentration in the bacterial cell culture media can range between about 1.0 mM and about 30.0 mM, such as between about 1.0 mM and about 20.0 mM, between about 1.0 mM and about 15.0 mM, between about 1.0 mM and about 10.0 mM, between about 1.0 mM and about 7.5 mM, between about 1.0 mM and about 5.0 mM, between about 4.0 mM and about 20.0 mM, between about 4.0 mM and about 15.0 mM, between about 4.0 mM and about 10.0 mM, between about 4.0 mM and about 7.5 mM, between about 10.0 mM and about 30.0 mM, between about 10.0 mM and about 25.0 mM, between about 10.0 mM and about 20.0 mM, between about 10.0 mM and about 15.0 mM, between about 15.0 mM and about 30.0 mM, between about 15.0 mM and about 25.0 mM, or between about 15.0 mM and about 20.0 mM. In a preferred embodiment, the total concentration of arginine in the bacterial cell culture media is between about 1.0 mM and about 20.0 mM, most preferably about 4.0 mM.

In an aspect of the invention, the total cysteine concentration in the bacterial cell culture media may be between about 0.1 mM and about 5.0 mM, such as between about 0.1 mM and about 4.5 mM, between about 0.1 mM and about 4.0 mM, between about 0.1 mM and about 3.5 mM, between about 0.1 mM and about 3.0 mM, between about 0.1 mM and about 2.5 mM, between about 0.4 mM and about 5.0 mM, between about 0.4 mM and about 4.5 mM, between about 0.4 mM and about 4.0 mM, between about 0.4 mM and about 3.5 mM, between about 0.4 mM and about 3.0 mM, between about 0.4 mM and about 2.5 mM, or between about 0.4 mM and about 2.0 mM. In a preferred embodiment, the total concentration of cysteine in the bacterial cell culture media is between about 0.1 mM and about 3.5 mM, most preferably about 0.4 mM.

In an aspect of the invention, the total serine concentration in the bacterial cell culture media may be between about 5.0 mM and about 75.0 mM, such as between about 5.0 mM and about 50.0 mM, between about 5.0 mM and about 40.0 mM, between about 5.0 mM and about 30.0 mM, between about 5.0 mM and about 20.0 mM, between about 5.0 mM and about 15.0 mM, between about 10.0 mM and about 75.0 mM, between about 10.0 mM and about 50.0 mM, between about 10.0 mM and about 40.0 mM, between about 10.0 mM and about 30.0 mM, between about 10.0 mM and about 20.0 mM, between about 15.0 mM and about 75.0 mM, between about 15.0 mM and about 50.0 mM, between about 15.0 mM and about 40.0 mM, between about 15.0 mM and about 30.0 mM, or between about 20.0 mM and about 50.0 mM. In a preferred embodiment, the total concentration of serine in the bacterial cell culture media is between about 5.0 mM and about 15.0 mM, most preferably about 7.5 mM.

In an aspect of the invention, the total glutamine concentration in the bacterial cell culture media may range between about 1.0 mM and about 30.0 mM, such as between about 1.0 mM and about 20.0 mM, between about 1.0 mM and about 15.0 mM, between about 1.0 mM and about 10.0 mM, between about 1.0 mM and about 7.5 mM, between about 1.0 mM and about 5.0 mM, between about 4.0 mM and about 20.0 mM, between about 4.0 mM and about 15.0 mM, between about 4.0 mM and about 10.0 mM, between about 4.0 mM and about 7.5 mM, between about 10.0 mM and about 30.0 mM, between about 10.0 mM and about 25.0 mM, between about 10.0 mM and about 20.0 mM, between about 10.0 mM and about 15.0 mM, between about 15.0 mM and about 30.0 mM, between about 15.0 mM and about 25.0 mM, or between about 15.0 mM and about 20.0 mM. In a preferred embodiment, the total concentration of glutamine in the bacterial cell culture media is between about 1.0 mM and about 20.0 mM, most preferably about 4.0 mM.

In an aspect of the invention, the total tyrosine concentration in the bacterial cell culture media can range between about 0.1 mM and about 5.0 mM, such as between about 0.1 mM and about 4.5 mM, between about 0.1 mM and about 4.0 mM, between about 0.1 mM and about 3.5 mM, between about 0.1 mM and about 3.0 mM, between about 0.1 mM and about 2.5 mM, between about 1.0 mM and about 5.0 mM, between about 1.0 mM and about 4.5 mM, between about 1.0 mM and about 4.0 mM, between about 1.0 mM and about 3.5 mM, between about 1.0 mM and about 3.0 mM, between about 1.0 mM and about 2.5 mM, or between about 1.0 mM and about 2.0 mM. In a preferred embodiment, the total concentration of tyrosine in the bacterial cell culture media is between about 1.0 mM and about 3.5 mM, most preferably about 2.9 mM or about 3.0 mM.

In an aspect of the invention, the total asparagine concentration in the bacterial cell culture media may be between about 5.0 mM and about 50.0 mM, such as between about 5.0 mM and about 40.0 mM, between about 5.0 mM and about 30.0 mM, between about 5.0 mM and about 25.0 mM, between about 5.0 mM and about 20.0 mM, between about 5.0 mM and about 15.0 mM, between about 5.0 mM and about 10.0 mM, between about 10.0 mM and about 50.0 mM, between about 10.0 mM and about 40.0 mM, between about 10.0 mM and about 30.0 mM, between about 10.0 mM and about 25.0 mM, between about 10.0 mM and about 20.0 mM, between about 15.0 mM and about 50.0 mM, between about 15.0 mM and about 40.0 mM, between about 15.0 mM and about 30.0 mM, between about 15.0 mM and about 25.0 mM, or between about 15.0 mM and about 20.0 mM. In a preferred embodiment, the total concentration of asparagine in the bacterial cell culture media is between about 10.0 mM and about 30.0 mM, most preferably about 20.0 mM.

In another aspect of the invention, the cell culture media does not contain asparagine.

The present inventors also found that potassium was a beneficial salt for the production of polysaccharides, which was independent of growth. Accordingly, in one aspect of the invention, the cell culture media comprises a potassium salt, such as potassium chloride or potassium sulfate.

In one embodiment, the concentration of potassium salt in the cell culture media may be between about 0.1 g/L and about 25 g/L, such as between about 0.1 g/L and about 20 g/L, between about 0.1 g/L and about 10 g/L, between about 0.1 g/L and about 5 g/L, between about 0.1 g/L and about 1.5 g/L, between about 0.1 g/L and about 1.25 g/L, between about 0.1 g/L and about 1.0 g/L, between about 0.1 g/L and about 0.9 g/L, between about 0.1 g/L and about 0.8 g/L, between about 0.1 g/L and about 0.7 g/L, between about 0.1 g/L and about 0.6 g/L, between about 0.1 g/L and about 0.5 g/L, between about 0.2 g/L and about 1.5 g/L, between about 0.2 g/L and about 1.25 g/L, between about 0.2 g/L and about 1.0 g/L, between about 0.2 g/L and about 0.9 g/L, between about 0.2 g/L and about 0.8 g/L, between about 0.2 g/L and about 0.7 g/L, between about 0.2 g/L and about 0.6 g/L, between about 0.2 g/L and about 0.5 g/L, between about 0.3 g/L and about 1.5 g/L, between about 0.3 g/L and about 1.25 g/L, between about 0.3 g/L and about 1.0 g/L, between about 0.3 g/L and about 0.9 g/L, between about 0.3 g/L and about 0.8 g/L, between about 0.3 g/L and about 0.7 g/L, between about 0.3 g/L and about 0.6 g/L, between about 0.3 g/L and about 0.5 g/L, between about 0.5 g/L and about 1.5 g/L, between about 0.5 g/L and about 1.25 g/L, or between about 0.5 g/L and about 1.0 g/L. In a preferred embodiment, the total concentration of potassium salt in the bacterial cell culture media is between about 0.2 g/L and about 1.25 g/L, most preferably about 0.9 g/L.

In an another embodiment, the concentration of potassium chloride is between 0.31 g/L and 24.31 g/L.

In one aspect of the invention, the cell culture media of the present invention contains a carbon source. Suitable carbon sources include glucose, dextrose, mannitol, lactose, sucrose, fructose, galactose, raffinose, xylose, and/or mannose. In a preferred embodiment, the carbon source is glucose.

The total concentration of the carbon source in the bacterial cell culture media can range between about 25 g/L to about 100 g/L, such as between about 25 g/L and about 90 g/L, between about 25 g/L and about 80 g/L, between about 25 g/L and about 70 g/L, between about 25 g/L and about 60 g/L, between about 25 g/L and about 50 g/L, between about 50 g/L and about 100 g/L, between about 50 g/L and about 90 g/L, between about 50 g/L and about 80 g/L, between about 50 g/L and about 70 g/L, between about 60 g/L and about 100 g/L, between about 60 g/L and about 90 g/L, between about 60 g/L and about 80 g/L, between about 70 g/L and about 100 g/L, or between about 70 g/L and about 90 g/L. In a preferred embodiment, the concentration of the carbon source in the culture medium is between about 25 g/L and about 80 g/L, most preferably about 50 g/L.

In another aspect, the cell culture media is modified to accommodate the sodium bicarbonate requirement of bacteria grown anaerobically. Some examples of polysaccharide-producing bacteria that are grown anaerobically include *S. agalactiae* and *S. pneumoniae*. In one embodiment, about 0.1 g/L to about 20 g/L of sodium bicarbonate is added to the media. For example, the sodium bicarbonate concentration may be between about 0.1 g/L and about 15 g/L, between about 0.1 g/L and about 10 g/L, between about 0.1 g/L and about 5.0 g/L, between about 0.1 g/L and about 3.0 g/L, between about 0.1 g/L and about 2.0 g/L, between about 0.1 g/L and about 1.25 g/L, between about 0.1 g/L and about 1.0 g/L, between about 0.1 g/L and about 0.9 g/L, between about 0.1 g/L and about 0.8 g/L, between about 0.1 g/L and about 0.7 g/L, between about 0.1 g/L and about 0.6 g/L, between about 0.1 g/L and about 0.5 g/L, between 0.5 g/L and about 20 g/L, between about 0.5 g/L and about 15 g/L, between about 0.5 g/L and about 10 g/L, between about 0.5 g/L and about 5.0 g/L, between about 0.5 g/L and about 3.0 g/L, between about 0.5 g/L and about 2.0 g/L, between about 0.5 g/L and about 1.25 g/L, between about 0.5 g/L and about 1.0 g/L, between about 0.5 g/L and about 0.9 g/L, between about 0.5 g/L and about 0.8 g/L, between about 0.5 g/L and about 0.7 g/L, between about 0.75 g/L and about 20 g/L, between about 0.75 g/L and about 15 g/L, between about 0.75 g/L and about 10 g/L, between about 0.75 g/L and about 5.0 g/L, between about 0.75 g/L and about 3.0 g/L, between about 0.75 g/L and about 2.0 g/L, between about 0.75 g/L and about 1.25 g/L, between about 0.75 g/L and about 1.0 g/L, or between about 0.75 g/L and about 0.9 g/L. Preferably, the sodium bicarbonate concentration is about 0.84 g/L, or between about 1.8 g/L and about 2.4 g/L.

In one aspect of the invention, the defined bacterial cell culture media comprises yeast extract. Yeast extracts suitable for use in the present invention may include yeast autolysate, ultrafiltered yeast extracts, and synthetic yeast extracts. In one aspect, the yeast extract is BD BBL (BD Biosciences), BD BACTO (BD Biosciences), HY YEST 412 (Kerry Group Services Ltd.), Y YEST 441 (Kerry, Inc. Kerry Group Services Ltd.), HY YEST 444 (Kerry Group Services Ltd.), or HY YEST 504 (Kerry Group Services Ltd.). In another aspect, the yeast extract is an ultrafiltered yeast extract, such as AMBERFERM 5902 (Sensient Technologies Corp.), BD DIFCO (BD Biosciences), HYPEP YE (Kerry Group Services Ltd.), or ULTRAPEP YE (Kerry Group Services Ltd.). In a further aspect, the yeast extract is a synthetic yeast extract, such as BD RECHARGE (BD Biosciences). Most preferably, the yeast extract is an ultrafiltered yeast extract, such as AMBERFERM 5902 (Sensient Technologies Corp.).

Concentrations of the yeast extract in the culture medium can be between about 1 g/L to about 50 g/L, such as between about 1 g/L and about 40 g/L, between about 1 g/L and about 30 g/L, between about 1 g/L and about 25 g/L, between about 1 g/L and about 20 g/L, between about 1 g/L and about 15 g/L, between about 1 g/L and about 10 g/L, between about 5 g/L and about 50 g/L, between about 5 g/L and about 40 g/L, between about 5 g/L and about 30 g/L, between about 5 g/L and about 25 g/L, between about 5 g/L and about 20 g/L, between about 5 g/L and about 15 g/L, between about 10 g/L and about 50 g/L, between about 10 g/L and about 40 g/L, between about 10 g/L and about 30 g/L, between about 10 g/L and about 35 g/L, between about 10 g/L and about 30 g/L, between about 10 g/L and about 25 g/L, between about 10 g/L and about 20 g/L, between about 15 g/L and about 50 g/L, between about 15 g/L and about 40 g/L, between about 15 g/L and about 30 g/L, or between about 15 g/L and about 25 g/L. In a preferred embodiment, the concentration of yeast extract in the culture medium is between about 5 g/L to about 25 g/L, most preferably about 10 g/L.

One aspect of the invention relates to a defined cell culture media comprising at least about 50 mM of amino acids, a potassium salt, a carbon source, and optionally, a yeast extract.

In one embodiment, the cell culture media comprises at least about 50 mM of amino acids, between about 5.0 mM and about 15.0 mM of glycine, between about 0.2 g/L and about 1.25 g/L of a potassium salt, between about 25 g/L and about 80 g/L of a carbon source, and between about 5 g/L to about 25 g/L of a yeast extract.

In a preferred embodiment, the cell culture media comprises at least about 60 mM of amino acids, about 7.5 mM of glycine, about 0.9 g/L of potassium chloride, 50 g/L of glucose, and about 10 g/L of an ultrafiltered yeast extract.

Furthermore, one of ordinary skill in the art will recognize that any of the conditions listed above may be used either singly or in various combinations with one another. By utilizing media formulation which exhibit one, some or all of the above characteristics, one of ordinary skill in the art will be able to optimize cell growth and/or viability and to maximize the production of polysaccharide.

Any of these media formulations disclosed in the present invention may optionally be supplemented as necessary with particular ions (such as sodium, chloride, calcium, magnesium, and phosphate), buffers, vitamins, trace elements (inorganic compounds usually present at very low final concentrations), amino acids, lipids, protein hydrolysates, or glucose or other energy source. These optional supplements may be added at the beginning of the culture or may be added at a later point in order to replenish depleted nutrients or for another reason. One of ordinary skill in the art will be aware of any desirable or necessary supplements that may be included in the disclosed media formulations.

In another aspect, the cultivation is carried out by any of the methods disclosed herein until the cell density, as determined by optical density (OD) at 600 nm, of the bacterial cell culture using the defined media of the invention is at least 9.0, such as at least 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0. In a preferred embodiment, the cultivation is carried out by any of the methods disclosed herein until the cell density is at least 9.0.

For polysaccharides that contain sialic acid such as GBS, polysaccharide yield may be determined by measuring sialic acid concentration. Sialic acid is released from cell bound polysaccharide by digesting pelleted cells by methods well-known in the art. The digest is assayed by anion exchange chromatography (AEX) via high performance liquid chromatography (HPLC). Polysaccharide concentration is then determined by multiplying the sialic acid value times a repeat unit weight conversion factor. For example, the conversion factor for each GBS serotype is as follows: Ia, Ib, and III=3.24; II and V=4.29; and IV=3.77.

In one aspect, the cultivation is carried out using any of the methods disclosed herein until the polysaccharide concentration, as determined by sialic acid concentration, of the bacterial cell culture using the defined media of the invention is at least about 250 mg/L, such as at least about 300 mg/L, 350 mg/L, 400 mg/L, 450 mg/L, 500 mg/L, 550 mg/L, 600 mg/L, 650 mg/L, 700 mg/L, 750 mg/L, 800 mg/L, 900 mg/L, 1000 mg/L, 1200 mg/L, 1500 mg/L or 2000 mg/L. In a preferred embodiment, the cultivation is carried out using any of the methods disclosed herein until the polysaccharide concentration is at least about 250 mg/L. In one aspect, the polysaccharide concentration, as determined by sialic acid concentration, of the bacterial cell culture using the defined media of the invention may be at least about 250 mg/L, such as at least about 300 mg/L, 350 mg/L, 400 mg/L, 450 mg/L, 500 mg/L, 550 mg/L, 600 mg/L, 650 mg/L, 700 mg/L, 750 mg/L, 800 mg/L, 900 mg/L, 1000 mg/L, 1200 mg/L, 1500 mg/L or 2000 mg/L. In a preferred embodiment, the polysaccharide concentration is at least about 250 mg/L.

Fermentation Methods

The present invention provides fermentation methods for cultivating polysaccharide-producing bacteria. In one aspect, the cultivation methods of the present invention are used in combination with the complex and defined media described herein to maximize polysaccharide production.

Seed Growth

In one embodiment, growth of polysaccharide-producing bacteria in the methods of the invention proceeds in at least two phases: seed growth and fermentation. A seed culture is first grown by inoculation from a stock culture, e.g., a working cell bank. The seed is used either to inoculate a second seed culture or to inoculate a relatively large fermentation culture. As is understood in the art, the number of seed cultures used may depend, for example, on the size and volume of the fermentation step.

Accordingly, in one aspect, the invention relates to a method of culturing polysaccharide-producing bacteria. The method includes culturing a polysaccharide-producing bacterial cell in a first culture medium under conditions that facilitate growth of the cell; inoculating a second culture medium with all or a portion of said first medium after said first culturing; culturing said inoculated second medium under conditions that facilitate cell growth and/or polysaccharide production. The method may further include isolating a polysaccharide from said second medium. In one embodiment, the polysaccharide-producing bacteria are grown in a first culture medium referred to as a seed culture. In one embodiment, the seed culture includes a culture medium as described above and an inoculation from a stock culture that was grown in the medium. In one embodiment, the first and second culture media are the same. In another embodiment, the first and second culture media are different.

The seed growth phase (or phases) is generally carried out to scale-up the quantity of the microorganism from a stored culture, so that it can be used as an inoculant for the fermentation phase. The volume and quantity of viable cells used to inoculate the fermentation culture can be controlled more accurately if taken from an actively growing culture (e.g., a seed culture), rather than if taken from a stored culture.

In addition, more than one (e.g., two or three) seed growth phases can be used to scale-up the quantity of polysaccharide-producing bacteria for inoculation of the fermentation medium. Alternatively, growth of polysaccharide-producing bacteria in the fermentation phase can proceed directly from the stored culture by direct inoculation, if desired.

To start the fermentation phase, a portion or all of a seed culture containing the polysaccharide-producing bacteria may be used to inoculate a fermentation culture medium. An appropriate concentration of seed culture to use to inoculate fermentation media can be determined by those of skill in this art.

Fermentation may be used to produce the maximum cell growth and/or polysaccharide production in a large-scale environment. In one embodiment, the polysaccharide-producing bacteria are grown as a fermentation culture. In one embodiment, the fermentation culture was inoculated from a seed culture that was grown in the first medium and the fermentation culture is carried out in a second medium. In one embodiment, the second medium may be the complex or defined media as described above. In another embodiment, the first medium and the second medium are the same.

Fed Batch Fermentation Process

In one embodiment, the polysaccharide-producing bacterial cell is cultured in a fed batch culture system using the complex and defined media described above. In a fed batch system, the culture is initiated with an inoculation of cells, supplemented with at least one nutrient added during the culture, and terminated with a single harvest of cells. In one embodiment, the nutrient is added at a constant rate.

In one aspect, the carbon source is the nutrient added during the culture. The carbon source may be any carbon source described above for the complex and/or defined media. In a preferred embodiment, the carbon source is glucose.

In an aspect of the invention, the amount of batched carbon source/amount of fed carbon source may be about 10%/90%, 15%/85%, 20%/80%, 25%/75%, or 30%/70%. For instance, in a preferred embodiment, 20% of the total concentration of the carbon source is batched and the remaining 80% is fed at a constant rate over the course of the culture. In another embodiment, 20% of the total concentration of the carbon source is batched and the remaining carbon source may also be fed at a non-constant rate over the course of the culture.

In yet another aspect, the fed batch fermentation process is carried out until the cell density, as determined by optical density (OD) at 600 nm, of the bacterial cell culture is at least 9.0, such as at least 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0. In a preferred embodiment, the fed batch fermentation process is carried out until the cell density is at least 9.0.

In yet another aspect, the cell density, as determined by optical density (OD) at 600 nm, of the bacterial cell culture by the fed batch culture system of the invention may be at least 9.0, such as at least 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0. In a preferred embodiment, the cell density is at least 9.0.

For polysaccharides that contain sialic acid such as GBS, polysaccharide yield may be determined by measuring sialic acid concentration. Sialic acid is released from cell bound polysaccharide by digesting pelleted cells by methods well-known in the art. The digest is assayed by anion exchange chromatography (AEX) via high performance liquid chromatography (HPLC). Polysaccharide concentration is then determined by multiplying the sialic acid value times a repeat unit weight conversion factor. For example, the conversion factor for each GBS serotype is as follows: Ia, Ib, and III=3.24; II and V=4.29; and IV=3.77. Polysaccharide yield for S. pneumoniae or other encapsulated bacteria may be quantified by first releasing the capsular polysaccharide from the cell wall by treatment with a detergent, such as sodium deoxycholic acid (DOC) or sodium N-lauryl-sarcosine (NLS); acid treatment at high temperature; base treatment; and/or mechanical lysis. The released polysaccharide in the crude lysate is then assayed against an authentic standard using size exclusion chromatography (SEC) HPLC.

In one aspect, the fed batch fermentation process is carried out until the polysaccharide concentration, as determined by sialic acid concentration, of the bacterial cell culture is at least about 250 mg/L, such as at least about 300 mg/L, 350 mg/L, 400 mg/L, 450 mg/L, 500 mg/L, 550 mg/L, 600 mg/L, 650 mg/L, 700 mg/L, 750 mg/L, 800 mg/L, 900 mg/L, 1000 mg/L, 1200 mg/L, 1500 mg/L or 2000 mg/L. In a preferred embodiment, the fed batch fermentation process is carried out until the polysaccharide concentration is at least about 250 mg/L.

In one aspect, the polysaccharide concentration, as determined by SEC HPLC, of the bacterial cell culture by the fed batch culture system of the invention may be at least about 250 mg/L, such as at least about 300 mg/L, 350 mg/L, 400 mg/L, 450 mg/L, 500 mg/L, 550 mg/L, 600 mg/L, 650 mg/L, 700 mg/L, 750 mg/L, 800 mg/L, 900 mg/L, 1000 mg/L, 1200 mg/L, 1500 mg/L or 2000 mg/L. In a preferred embodiment, the polysaccharide concentration is at least about 250 mg/L.

Perfusion Fermentation Process

In one embodiment, the polysaccharide-producing bacterial cell is cultured in a perfusion culture system. The inventors discovered that maximal polysaccharide production may be obtained in a perfusion culture using the complex and defined media described above. An advantage of a perfusion system is that fresh media may be added continuously. In addition, metabolic waste products may be removed during production while maintaining cell viability in the system.

The perfusion culture system may include providing fresh medium to the cells while simultaneously removing spent medium that is substantially free of cells or includes a substantially lower cell concentration than that in the bioreactor. In a perfusion culture, cells can be retained by, for example, filtration, ultrasonic filtration, centrifugation, or sedimentation.

In one embodiment, the spent media is separated from the cells and removed, while retaining the cells in or returning the cells to the bioreactor. The separation step may be a normal flow filter and/or a tangential flow filter. In one embodiment, said filtration system comprises a hollow fiber filter. In another embodiment, said filtration system comprises a flat-sheet cassette. In another embodiment, the cells are separated from the spent medium by a centrifugation step. In another embodiment, the cells are separated from the spent medium by an ultrasonic separation step. In another embodiment, the cells are separated from the spent medium via a sedimentation system.

In one embodiment the rate of perfusion may be between about 0.07 VVH to about 2.00 VVH, such as between about between about 0.07 VVH to about 1.33 VVH, between about 0.07 VVH to about 1.20 VVH, between about 0.07 VVH to about 1.07 VVH, between about 0.07 VVH to about 0.93 VVH, between about 0.07 VVH to about 0.80 VVH, between about 0.07 VVH to about 0.67 VVH, between about 0.07 VVH to about 0.53 VVH, between about 0.07 VVH to about 0.40 VVH, between about 0.07 VVH to about 0.27 VVH, between about 0.13 VVH to about 2.00 VVH, between about 0.13 VVH to about 1.33 VVH, between about 0.13 VVH to about 1.20 VVH, between about 0.13 VVH to about 1.07 VVH, between about 0.13 VVH to about 0.93 VVH, between about 0.13 VVH to about 0.80 VVH, between about 0.13 VVH to about 0.67 VVH, between about 0.13 VVH to about 0.53 VVH, between about 0.13 VVH to about 0.40 VVH, between about 0.13 VVH to about 0.27 VVH, between about 0.27 VVH to about 2.00 VVH, between about 0.27 VVH to about 1.33 VVH, between about 0.27 VVH to about 1.20 VVH, between about 0.27 VVH to about 1.07 VVH, between about 0.27 VVH to about 0.93 VVH, between about 0.27 VVH to about 0.80 VVH, between about 0.27 VVH to about 0.67 VVH, between about 0.27 VVH to about 0.53 VVH, between about 0.27 VVH to about 0.40 VVH, between about 0.40 VVH to about 2.00 VVH, between about 0.40 VVH to about 1.33 VVH, between about 0.40 VVH to about 1.20 VVH, between about 0.40 VVH to about 1.07 VVH, between about 0.40 VVH to about 0.93 VVH, between about 0.40 VVH to about 0.80 VVH, between about 0.40 VVH to about 0.67 VVH, between about 0.53 VVH to about 2.00 VVH, between about 0.53 VVH to about 1.33 VVH, between about 0.53 VVH to about 1.20 VVH, between about 0.53 VVH to about 1.07 VVH, between about 0.53 VVH to about 0.93 VVH, between about 0.53 VVH to about 0.80 VVH, between about 0.53 VVH to about 0.67 VVH, between about 0.67 VVH to about 2.00 VVH, between about 0.67 VVH to about 1.33 VVH, between about 0.67 VVH to about 1.20 VVH, between about 0.67 VVH to about 1.07 VVH, between about 0.67 VVH to about 0.93 VVH, or between about 0.67 VVH to about 0.80 VVH. In one embodiment, the rate of perfusion is between about 0.67 VVH to about 1.33 VVH, preferably about 1.20 VVH.

In one aspect, the duration of the perfusion culture may be between about 1 hour and about 15 hours, such as between about 1 hour and about 14 hours, between about 1 hour and about 13 hours, between about 1 hour and about 12 hours, between about 1 hour and about 11 hours, between about 1 hour and about 10 hours, between about 1 hour and about 9 hours, between about 1 hour and about 8 hours, between about 1 hour and about 7 hours, between about 1 hour and about 6 hours, between about 1 hour and about 5 hours, between about 5 hours and about 15 hours, between about 5 hours and about 14 hours, between about 5 hours and about 13 hours, between about 5 hours and about 12 hours, between about 5 hours and about 11 hours, between about 5 hours and about 10 hours, between about 5 hours and about 9 hours, between about 5 hours and about 8 hours, or between about 5 hours and about 7 hours. In one embodiment, the duration of the perfusion culture is between about 1 hour and about 10 hours, preferably about 7 hours.

In one particular aspect, the rate of perfusion may be varied (increased or decreased) for the duration of the culture. In one embodiment, the perfusion system starts at a first rate and the rate is increased to a second rate. In another embodiment, the perfusion system starts at a first rate and the rate is decreased to a second rate. In an additional embodiment, the rate of perfusion may be changed multiple times.

In one aspect, the rate of perfusion is kept constant for the duration of the culture.

In another aspect of the invention, the cell growth in the perfusion system may be at least 1.1-fold, such 1.2, 1.3, 1.4, 1.5, 1.6, 1.7, 1.8, 1.9, 2.0, 2.1, 2.2, 2.3, 2.4 or 2.5-fold, greater than in a batch fermentation system. In a preferred embodiment, the cell growth in the perfusion system is at least 2-fold greater than in a batch fermentation system.

In yet another aspect, the perfusion fermentation process is carried out until the cell density, as determined by optical density (OD) at 600 nm, of the bacterial cell culture is at least 20.0, such as at least 25.0, 30.0, 35.0, 40.0, 45.0 50.0, 55.0, or 60.0. In a preferred embodiment, the perfusion fermentation process is carried out until the cell density is at least 20.0.

In yet another aspect, the cell density, as determined by optical density (OD) at 600 nm, of the bacterial cell culture by the perfusion system of the invention may be at least 20.0, such as at least 25.0, 30.0, 35.0, 40.0, 45.0 50.0, 55.0, or 60.0. In a preferred embodiment, the cell density is at least 20.0.

In another aspect of the invention, the polysaccharide concentration in the perfusion system is at least 1.5-fold, such as at least 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, or 3.5-fold, greater than in a batch fermentation system.

In a preferred embodiment, the polysaccharide concentration in the perfusion system is at least 2-fold greater than in a batch fermentation system.

For polysaccharides that contain sialic acid, such as GBS, polysaccharide yield may be determined by measuring sialic acid concentration. Sialic acid is released from cell bound polysaccharide by digesting pelleted cells by methods well-known in the art. The digest is assayed by anion exchange chromatography (AEX) via high performance liquid chromatography (HPLC). Polysaccharide concentration is then determined by multiplying the sialic acid value times a repeat unit weight conversion factor. For example, the conversion factor for each GBS serotype is as follows: Ia, Ib, and III=3.24; II and V=4.29; and IV=3.77. Polysaccharide yield for *S. pneumoniae* or other encapsulated bacteria may be quantified by first releasing the capsular polysaccharide from the cell wall by treatment with a detergent, such as sodium deoxycholic acid (DOC) or sodium N-lauryl-sarcosine (NLS); acid treatment at high temperature; base treatment; and/or mechanical lysis. The released polysaccharide in the crude lysate is then assayed against an authentic standard using size exclusion chromatography (SEC) HPLC.

In one aspect, the perfusion fermentation process is carried out until the polysaccharide concentration, as determined by sialic acid concentration, of the bacterial cell culture is at least about 600 mg/L, such as at least about 650 mg/L; 700 mg/L; 750 mg/L; 800 mg/L, 850 mg/L; 900 mg/L; 950 mg/L; 1,000 mg/L; 1,500 mg/L; or 2,000 mg/L. In a preferred embodiment, perfusion fermentation process is carried out until the polysaccharide concentration is at least about 600 mg/L.

In one aspect, the polysaccharide concentration, as determined by SEC HPLC, of the bacterial cell culture by the perfusion system of the invention may be at least about 600 mg/L, such as at least about 650 mg/L; 700 mg/L; 750 mg/L; 800 mg/L, 850 mg/L; 900 mg/L; 950 mg/L; 1,000 mg/L; 1,500 mg/L; or 2,000 mg/L. In a preferred embodiment, the polysaccharide concentration is at least about 600 mg/L.

EXAMPLES

The following examples demonstrate some embodiments of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. All parts and percents referred to herein are on a weight basis and all temperatures are expressed in degrees centigrade unless otherwise specified.

Furthermore, the following examples were carried out using standard techniques, which are well known and routine to those of skill in the art, except where otherwise described in detail. As noted above, the following examples are presented for illustrative purpose, and should not be construed in any way limiting the scope of this invention.

Example 1: A Defined Medium of the Invention

Applicant's proprietary, mammalian defined cell culture medium ("R17") was modified for growth of *Streptococcus pneumoniae* to create "Modified AS3" medium (also referred to as "mAS3"). The Modified AS3 medium was formulated with the components of Table 3 below. The media prepared for serotypes 4, 5, 6A, 6B, 14, and 23F was formulated with 30 g/L of dextrose and 0.6 g/L of magnesium sulfate. In the case of serotypes 1, 3, 6B, 7F, 9V, 18C, 19A, and 19F, 30 g/L dextrose was added to the media in the reactor.

TABLE 3

| Modified AS3 Medium | |
|---|---|
| Component | Concentration (g/L) |
| R-17 dry powder | 15.56 g/L |
| L-tyrosine disodium salt, dihydrate | 0.643 g/L |
| Dextrose anhydrous | 25 g/L |
| Sodium chloride | 1.1 g/L |
| 300 mM acidic cystine stock | 3.75 mL/L |
| L-Asparagine monohydrate | 2.25 g/L |
| L-Glutamine | 1.17 g/L |
| 1 mM Ferrous sulfate stock | 15 mL/L |
| Trace elements E | 1 mL/L |
| Magnesium sulfate heptahydrate | 1.23 g/L |

A full accounting of the composition of the amino acids, vitamins and salts in the R17 powder is provided in Table 4 below.

TABLE 4

Composition of R17 Powder

| Amino Acids | g/L | mM |
|---|---|---|
| alanine | 0.02 | 0.20 |
| arginine | 0.70 | 4.00 |
| aspartic acid | 0.22 | 1.65 |
| cysteine•HCl•$H_2O$ | 0.07 | 0.40 |
| monosodium glutamate | 0.03 | 0.20 |
| glycine | 0.12 | 1.54 |
| histidine•HCl•$H_2O$ | 0.47 | 2.26 |
| isoleucine | 0.57 | 4.36 |
| leucine | 1.03 | 7.87 |
| lysine•HCl | 1.40 | 7.70 |
| methionine | 0.39 | 2.60 |
| phenylalanine | 0.51 | 3.07 |
| proline | 0.54 | 4.69 |
| serine | 1.05 | 10.02 |
| threonine | 0.56 | 4.75 |
| tryptophan | 0.27 | 1.34 |
| valine | 0.75 | 6.40 |

| Other Components | g/L | nM |
|---|---|---|
| linoleic acid | 0.0003 | 1.04 |
| thioctic acid | 0.0007 | 3.48 |
| D-glucose (Dextrose) | 5.00 | 83.33 |
| Sodium pyruvate | 0.06 | 0.50 |

| Inorganic Salts | g/L | mM |
|---|---|---|
| $CaCl_2$ | 0.12 | 1.05 |
| KCl | 0.31 | 4.19 |
| $Na_2HPO_4$ | 0.06 | 0.40 |
| $NaH_2PO_4•H_2O$ | 0.65 | 4.68 |
| $MgCl_2$ | 0.03 | 0.30 |
| $MgSO_4$ | 0.14 | 1.15 |

| Trace Elements | µg/L | nM |
|---|---|---|
| Sodium Selenite | 69.16 | 400.00 |
| $CuSO_4$ | 10.24 | 64.00 |
| $CuSO_4•5H_2O$ | 99.88 | 400.00 |
| $FeSO_4•7H_2O$ | 4170 | 15000 |
| $MnSO_4•H_2O$ | 33.80 | 200.00 |
| $Na_2SiO_3•9H_2O$ | 284.07 | 1000 |
| $(NH_4)_6Mo_7O_{24}•4H_2O$ | 247.20 | 200.00 |
| $NH_4VO_3$ | 2.34 | 20.00 |
| $NiSO_4•6H_2O$ | 5.26 | 20.00 |
| $SnCl_2•2H_2O$ | 0.90 | 4.00 |
| $AlCl_3•6H_2O$ | 0.97 | 4.00 |
| KBr | 0.48 | 4.00 |
| $CrCl_3$ | 15.83 | 100.00 |
| NaF | 0.17 | 4.00 |
| $GeO_2$ | 0.42 | 4.00 |
| KI | 33.20 | 200.00 |
| RbCl | 0.48 | 4.00 |
| $H_3BO_3$ | 12.37 | 200.00 |
| LiCl | 0.17 | 4.00 |

| Vitamins | g/L | mM |
|---|---|---|
| biotin | 0.003 | 0.01 |
| calcium pantothenate | 0.02 | 0.05 |
| choline chloride | 0.16 | 1.14 |
| folic acid | 0.03 | 0.06 |
| inositol | 0.16 | 0.91 |
| nicotinamide | 0.03 | 0.22 |
| pyridoxal•HCl | 0.002 | 0.01 |
| pyridoxine•HCl | 0.004 | 0.18 |
| riboflavin | 0.002 | 0.01 |
| thiamine•HCl | 0.04 | 0.12 |
| vitamin B12 | 0.02 | 0.02 |

Batch fermentation was performed in a 2 L bioreactor with temperature control at 36° C. and pH control at 7.0 with NaOH used as base titrant. The fermentor was inerted with $N_2$ overlay for serotypes 1, 3, 4, 6A, 6B, 7F, 9V, 18C, 19A, and 19F and with air for serotypes 6B(2), 14 and 23F; no overlay was used for serotype 5. The fermentation was stirred at 200 RPM. Results are shown in Table 5 below.

TABLE 5

S. pneumoniae Growth and Polysaccharide Production in Modified AS3 Medium

| Serotype | Growth OD600 | Polysaccharide (g/L) |
|---|---|---|
| 1 | 9.1 | 1.38 |
| 3 | 11.5 | 3.19 |
| 4 | 9.5 | 0.50 |
| 5 | 7.5 | 0.40 |
| 6A | 6.6 | 1.10 |
| 6B | 6.0 | 2.00 |
| 6B(2) | 6.3 | 1.20 |
| 7F | 8.0 | 0.70 |
| 9V | 7.4 | 0.54 |
| 14 | 6.8 | 1.10 |
| 18C | 7.0 | 0.97 |
| 19A | 5.0 | 2.40 |
| 19F | 5.5 | 0.86 |
| 23F | 6.5 | 1.10 |

The thirteen S. pneumoniae serotypes were successfully grown in a batch culture using the chemically defined Modified AS3 medium.

Example 2: Comparison of Commercially Available Defined Medium to a Defined Medium of the Invention Eagle's minimum essential medium (EMEM), a commercially available defined cell culture medium, was tested in comparison to R17 using various serotypes of GBS. The formulation of each was modified from the label instructions to accommodate the sodium bicarbonate requirement of GBS grown anaerobically. Each medium was also supplemented with a high concentration of glucose to support the higher cell density achievable in bacterial cultures. The formulation for EMEM modified as a bacterial medium ("bacterial EMEM") was as follows: 20.2 g/L EMEM powder, 1.17 g/L L-glutamine, 0.84 g/L sodium bicarbonate and 80 g/L glucose. The composition of GBS mAS3mAS3 (as described in Example 1) was customized for GBS growth (hereinafter "GBS mAS3") as follows: 0.21 g/L L-cysteine HCl (instead of 300 mM acidic cystine stock), 2 mL/L (instead of 1 mL/L) Trace Element E 1000X, 0.84 g/L sodium bicarbonate and 80 g/L glucose (instead of 25 g/L dextrose anhydrous).

Fermentation was performed at 10 L bioreactor scale with temperature control at 37° C. and pH control at 7.0 with NaOH used as base titrant. The fermentor was inerted with $N_2$ overlay at 0.1 vvm with respect to the batch volume; the fermentation was stirred with agitation sufficient to achieve a kLa of 1 $hr^{-1}$. Results are shown in Table 6 below.

TABLE 6

Comparison of Bacterial EMEM and GBS mAS3

| | Growth $OD_{600}$ | | Polysaccharide (mg/L) | |
|---|---|---|---|---|
| GBS Serotype | Bacterial EMEM | GBS mAS3 | Bacterial EMEM | GBS mAS3 |
| Ia | 3.9 | 8.9 | 70 | 750 |
| Ib | 3.6 | 8.3 | 90 | 270 |
| II | 3.1 | 9.7 | 60 | 190 |
| III | 3.7 | 5.1 | 210 | 270 |
| IV | 3.6 | 8.2 | 70 | 260 |

TABLE 6-continued

Comparison of Bacterial EMEM and GBS mAS3

| GBS Serotype | Growth OD$_{600}$ | | Polysaccharide (mg/L) | |
|---|---|---|---|---|
| | Bacterial EMEM | GBS mAS3 | Bacterial EMEM | GBS mAS3 |
| V | 3.8 | 9.6 | 50 | 220 |

GBS mAS3 medium showed surprising superiority to the bacterial EMEM medium in both growth and polysaccharide concentration.

Example 3: Comparison of a Complex Medium to a Defined Medium of the Invention

Modified AS3 medium as described in Example 1 and a soy hydrolysate-based complex medium (BPDv3) were compared for various serotypes of S. pneumoniae. BPDv3 was composed of 28 g/L HYPEP1510 (Kerry Group Services Ltd.), 54 g/L glucose, 3.5 g/L NaCl, 0.7 g/L KH$_2$PO$_4$, 0.0182 g/L CaCl$_2$.2H$_2$O, 1 g/L MgSO$_4$.7H$_2$O, 0.84 g/L NaHCO$_3$, 3 g/L ammonium chloride, 0.25 g/L uridine, 0.25 g/L adenosine, 0.03 g/L niacinamide, 0.03 g/L pyridoxine HCl, 0.0075 g/L pantothenic acid and 0.003 g/L PABA. Medium for serotype 12F was supplemented with 1 g/L monosodium glutamate, and medium for serotype 8 was modified to contain 0.5 g/L ammonium chloride and 36 g/L glucose. Although polysaccharide titer was not consistently improved in the Modified AS3 medium as compared to the complex medium, the Modified AS3 medium showed improved growth in almost all serotypes (see Table 7).

TABLE 7

Comparison of Modified R17 Medium and Complex Medium

| S. pneumoniae Serotype | Growth (OD$_{600}$) | | Polysaccharide (mg/L) | |
|---|---|---|---|---|
| | Modified AS3 | BPDv3 | Modified AS3 | BPDv3 |
| 8 | 9.2 | 5.2 | 2630 | 2310 |
| 10A | 12.9 | 8.1 | 790 | 890 |
| 11A | 14.8 | 7.3 | 1210 | 1140 |
| 12F | 9.4 | 10.0 | 910 | 2130 |
| 15B | 12.5 | 7.8 | 1170 | 1900 |
| 22F | 14.4 | 6.4 | 1740 | 1350 |
| 33F | 14.4 | 11.5 | 2580 | 3430 |

Example 4: Amino Acid Consumption

An analysis of amino acid consumption during the course of GBS serotype III fermentation was performed to determine if amino acids were depleted. An analysis of the concentration of amino acids in the GBS mAS3 (as in Example 2) prior to inoculation and at harvest is presented in Table 8.

TABLE 8

Amino Acid Consumption

| Amino Acid | Initial (mM) | Harvest (mM) |
|---|---|---|
| Alanine | 0 | 0.6 |
| Arginine | 3.6 | 0 |

TABLE 8-continued

Amino Acid Consumption

| Amino Acid | Initial (mM) | Harvest (mM) |
|---|---|---|
| Aspartic acid | 1.8 | 1.8 |
| Asparagine | 16.7 | 14.9 |
| Cysteine | < | < |
| Glutamic acid | 0.3 | 1.5 |
| Glutamine | 9.8 | 6.2 |
| Glycine | 1.4 | 0.2 |
| Histidine | 2.3 | 2.2 |
| Isoleucine | 4.6 | 4 |
| Leucine | 8.6 | 8 |
| Lysine | 9.3 | 6.2 |
| Methionine | 2.9 | 2.6 |
| Phenylalanine | 3.4 | 3.1 |
| Proline | 5.1 | 5.1 |
| Serine | 10.8 | 0 |
| Threonine | 5.8 | 6.2 |
| Tryptophan | 1.5 | 1.5 |
| Tyrosine | 1.8 | 1.9 |
| Valine | 6.9 | 6.1 |

Although predicted required amino acids were not depleted, four amino acids for which S. agalactiae is presumably prototrophic were. Arginine, glycine, and serine were depleted to less than the limit of quantification. Cysteine, which is difficult to measure by the HPLC method, was not detected at either sample time. All other amino acids were still in excess at harvest.

The four depleted amino acids were then supplemented to GBS mAS3 medium in fermentation of various GBS serotypes at 4× concentration with respect to the basic powder R17 formulation (16 mM arg, 1.6 mM cys, 6 mM gly, and 40 mM ser). Results are shown in Table 9 below.

TABLE 9

Comparison of GBS mAS3 and GBS mAS3 Supplemented with Depleted Amino Acids

| GBS Serotype | Growth (OD$_{600}$) | | Polysaccharide (mg/L) | |
|---|---|---|---|---|
| | GBS mAS3 | Supplemented CGRS | GBS mAS3 | Supplemented CGRS |
| Ia | 9.6 | 10.0 | 670 | 430 |
| Ib | 9.0 | 17.8 | 230 | 360 |
| II | 8.6 | 13.9 | 110 | 140 |
| III | 5.1 | 10.8 | 260 | 340 |
| IV | 7.4 | 10.7 | 330 | 270 |
| V | 9.4 | 16.4 | 140 | 210 |

A significant improvement in growth was observed in all six serotypes tested with supplemented CGRS medium. Although the polysaccharide titers did not increase for all serotypes, the growth improvement encouraged further testing.

Example 5: Further Analysis of Depleted Amino Acids

The importance of each of the depleted amino acid to the improvement in growth was assessed in an experiment in which each of the four was sequentially deleted from the medium using GBS serotype V as a model. Glycine was unexpectedly found to be the sole contributor to improved growth (see Table 10).

TABLE 10

Sequential Deletion of Supplemented Amino Acids

| Amino Acids Added | Growth (OD600) | Polysaccharide (mg/L) |
|---|---|---|
| None | 9.7 | 240 |
| CGRS | 15.2 | 330 |
| GRS | 15.6 | 330 |
| CRS | 9.6 | 200 |
| CGS | 14.4 | 350 |
| CGRS | 15.1 | 360 |

This was confirmed in a follow up study in which each of the four amino acids were supplemented individually, again using GBS serotype V as a model. The study confirmed that glycine was the only amino acid of the four depleted amino acids that improved growth and polysaccharide production (see Table 11).

TABLE 11

Supplementation of Individual Amino Acids

| Amino Acid(s) Added | Growth (OD600) | Polysaccharide (mg/L) |
|---|---|---|
| None | 9.7 | 240 |
| CGRS | 15.2 | 330 |
| G only | 13.1 | 440 |
| A only | 8.8 | 280 |
| C only | 9.0 | 310 |
| S only | 9.3 | 280 |

The importance of the added glycine as a sole supplement was then tested in several GBS serotypes. Performance in GBS mAS3, GBS mAS3 supplemented with all four amino acids, and GBS mAS3 supplemented with only glycine was compared. Results are shown in Table 12 below.

TABLE 12

Comparison of GBS mAS3, GBS mAS3 Supplemented with All Four Amino Acids, and GBS mAS3 Supplemented with Only Glycine

| | Growth (OD$_{600}$) | | | Polysaccharide (mg/L) | | |
|---|---|---|---|---|---|---|
| GBS Serotype | GBS mAS3 | Supplemented CGRS | Glycine | GBS mAS3 | Supplemented CGRS | Glycine |
| Ia | 9.6 | 10.0 | 12.1 | 670 | 430 | 850 |
| Ib | 9.0 | 17.8 | 11.1 | 230 | 360 | 480 |
| II | 8.6 | 13.9 | 12.1 | 110 | 140 | 403 |
| III | 5.1 | 10.8 | 10.1 | 260 | 340 | 569 |
| IV | 7.4 | 10.7 | 10.9 | 330 | 270 | 530 |
| V | 9.4 | 16.4 | 15.7 | 140 | 210 | 290 |

In general, sole supplementation with glycine was sufficient to improve growth in a manner about equivalent to supplementation with all four amino acids. However, sole supplementation with glycine surprisingly produced higher polysaccharide titer than GBS mAS3 and supplementation with all four amino acids.

Example 6: Comparison of Glycine Concentrations

In view of the unexpectedly high production of polysaccharides with the addition of glycine alone, an experiment was conducted to determine if the maximal growth and polysaccharide titer was obtained with the addition of 6 mM glycine to the GBS mAS3 formulation. The experiment compared the addition of from 0.15 mM to 123.2 mM glycine using GBS serotype V as a model. The data in Table 13 below show the addition of as little as 1.5 mM glycine or as much as 61.6 mM supports the same improvement in polysaccharide titer as seen with the addition of 6 mM glycine.

TABLE 13

Comparison of Glycine Concentrations

| Glycine Concentration (mM) | Growth (OD600) | Polysaccharide (mg/L) |
|---|---|---|
| 0 | 11.6 | 334 |
| 0.15 | 11.9 | 356 |
| 1.5 | 16.1 | 446 |
| 3.1 | 18.5 | 521 |
| 6.2 | 19.6 | 455 |
| 15.4 | 18.4 | 421 |
| 30.8 | 18.5 | 396 |
| 61.6 | 19.5 | 381 |
| 123.2 | 0 | 0 |

Example 7: Determining Nonessential Components of the GBS mAS3 Medium

The GBS mAS3 formulation and its glycine containing derivatives in Example 56 contained 80 g/L glucose to assure that the carbon source would be in excess throughout and at the end of the fermentation. In general, when growth and polysaccharide production had ceased, about 30 g/L glucose remained unconsumed (data not shown). Therefore, an experiment was conducted to determine if a more efficient medium could be achieved. Glycine-supplemented GBS mAS3 media with glucose concentrations of 80 g/L, 70 g/L, 60 g/L, and 50 g/L were tested with GBS serotype V as a model. The data in Table 14 below show that a glucose concentration of 50 g/L leaves no residual glucose but also does not compromise polysaccharide titer.

TABLE 14

Comparison of Glucose Concentrations

| Batched Glucose (g/L) | Growth (OD600) | Polysaccharide (mg/L) | Residual Glucose (g/L) |
|---|---|---|---|
| 80 | 17.6 | 410 | 28 |
| 70 | 18.2 | 420 | 17 |
| 60 | 18.8 | 430 | 10 |
| 50 | 19.4 | 420 | 0 |

Similarly, the importance of all amino acids and salts added to the R17 powder was examined by omitting each, one at a time, in a drop out experiment. The work was performed with GBS serotype V in glycine-supplemented GBS mAS3 medium. The data in Table 15 below indicate that tyrosine, glutamine, and cysteine are essential for growth, whereas asparagine is not, and all salts are nonessential.

TABLE 15

Drop Out of Amino Acids and Salts

| Component Deleted | Growth (OD600) | Polysaccharide (mg/L) |
|---|---|---|
| None | 12.7 | 570 |

TABLE 15-continued

Drop Out of Amino Acids and Salts

| Component Deleted | Growth (OD600) | Polysaccharide (mg/L) |
|---|---|---|
| Asn | 12.5 | 600 |
| Gln | 1.0 | 40 |
| Tyr | 0.2 | 10 |
| Cys | 6.2 | 290 |
| None | 13.2 | 510 |
| Magnesium sulfate | 13.5 | 540 |
| Ferrous sulfate | 12.3 | 510 |
| Trace elements E | 13.1 | 500 |
| Sodium chloride | 13.1 | 520 |

Example 8: Consumption of Vitamins and Salts/Trace Elements

An assessment of residual vitamins and salts/trace elements versus starting concentrations was done in glycine-supplemented GBS mAS3 media using GBS serotype III as a model. A total of 13 vitamins were examined: biotin, choline cyanocobalamin, folic acid, niacin, niacinamide, nicotinamide, p-aminobenzoic acid, panthotenic acid, pyridoxal, pyridoxamine, pyridoxine, riboflavin, and thiamine. Twelve showed no significant change in concentration during fermentation. Niacinamide was found to be depleted to zero during the course of the fermentation, but an accompanying accumulation of niacin would indicate that this vitamin family is not depleted (data not shown).

Thirty-two salts and trace elements were analyzed. Eighteen of these were below the limits of detection. Those 18 are as follows: silver, aluminum, arsenic, beryllium, cadmium, chromium, copper, mercury, lithium, manganese, nickel, lead, rubidium, selenium, tin, titanium, thallium, and vanadium. Of the 14 detectable salts and trace elements, 12 showed no substantial decline in concentration from initial inoculation of the medium to after harvest (see Table 16). Phosphorous and potassium were the two that showed a decline in concentration. The decline in phosphorous concentration was expected as it is consumed for cell growth, but it was not growth limiting since it remained in excess at harvest. The decline in potassium concentration, however, was unexpected.

TABLE 16

Salts and Trace Elements Consumption

| | Initial (mg/L) | Harvest (mg/L) |
|---|---|---|
| Boron | 1.5 | 1.6 |
| Barium | 4.4 | 4.0 |
| Calcium | 36.1 | 23.4 |
| Cobalt | 0.9 | 0.8 |
| Iron | 0.8 | 0.7 |
| Potassium | 292.0 | 22.0 |
| Magnesium | 138.0 | 121.0 |
| Molybdenum | 0.1 | 0.1 |
| Sodium | 1134.0 | 10851.0 |
| Phosphorous | 159.0 | 44.0 |
| Sulfur | 303.0 | 349.0 |
| Silicon | 0.0 | 1.9 |
| Strontium | 0.1 | 0.1 |
| Zinc | 4.1 | 4.4 |

The data provoked two studies in which the effect of adding an additional 2-fold amount of potassium chloride (0.6 g/L additional to the 0.31 g/L R17 powder) to the glycine-supplemented GBS mAS3 media in the fermentation of GBS serotype III was examined. The results shown in Table 17 indicate that the increase in KCl concentration was beneficial for polysaccharide titer in a growth independent fashion.

TABLE 17

Supplementation with KCl

| Study # | KCl concentration (g/L) | Growth (OD600) | Polysaccharide (mg/L) |
|---|---|---|---|
| 1 | 0.31 | 11.4 | 434 |
|   | 0.91 | 11.2 | 594 |
| 2 | 0.31 | 10.6 | 612 |
|   | 0.91 | 12.2 | 755 |

An additional study examined a fuller range of KCl concentrations (from 0.03 g/L to 24 g/L) additional to the 0.31 g/l KCl contained in the R17 basal powder) for their effect on growth and polysaccharide synthesis. The results are shown in Table 18 which indicate KCl concentrations of from 0.3 to 24 g/L additional to R17 powder confer improved growth and polysaccharide production.

TABLE 18

Supplementation of Glycine-Containing R17 with a Range of KCl Concentrations

| Additional KCl added (g/L) | Growth (OD600) | Polysaccharide (mg/L) |
|---|---|---|
| 0 | 12.3 | 308 |
| 0.03 | 15.3 | 347 |
| 0.3 | 17.8 | 382 |
| 0.6 | 18.2 | 387 |
| 1.2 | 19.5 | 406 |
| 3.0 | 19.7 | 402 |
| 17.0 | 19.7 | 432 |
| 12.0 | 17.1 | 370 |
| 24.0 | 17.9 | 382 |

Example 9: Formulation of mAS3opt50 Medium

A medium was configured to incorporate the increases in glycine and KCl, decrease in glucose concentration, and omission of magnesium, asparagine, and NaCl ("mAS3opt50") in GBS mAS3 medium. The new formulation was tested in comparison to GBS mAS3 medium for six GBS serotypes. As shown in Table 19, the reformulated medium affords substantially improved growth and concomitant polysaccharide titers.

TABLE 19

Comparison of GBS mAS3 and mAS3opt50

| GBS Serotype | Growth ($OD_{600}$) | | Polysaccharide (mg/L) | |
|---|---|---|---|---|
| | GBS mAS3 | mAS3opt50 | GBS mAS3 | mAS3opt50 |
| Ia | 8.9 | 18.6 | 750 | 930 |
| Ib | 8.3 | 19.3 | 270 | 560 |
| II | 9.7 | 17.0 | 190 | 440 |
| III | 5.1 | 13.9 | 270 | 750 |
| IV | 8.2 | 10.4 | 260 | 360 |
| V | 9.6 | 18.0 | 220 | 390 |

Example 10: Contribution of Glycine and KCl to Polysaccharide Yield in mAS3opt50

A drop out approach was used to demonstrate the importance of the glycine and KCl supplementation to polysaccharide yield in the mAS3opt50 medium. The data shown in Table 20 clearly indicates that each is important in supporting high yield.

TABLE 20

Drop Out of Glycine and KCl in mAS3opt50

| GBS Serotype | Growth ($OD_{600}$) | | | Polysaccharide (mg/L) | | |
|---|---|---|---|---|---|---|
| | mAS3opt50 | -glycine | -KCl | mAS3opt50 | -glycine | -KCl |
| Ia | 18.6 | 13.2 | 15.6 | 930 | 780 | 840 |
| Ib | 17.5 | 8.4 | 12.2 | 580 | 300 | 440 |
| II | 12.9 | 8.8 | 12.3 | 375 | 206 | 311 |
| III | 13.5 | 10.5 | 12.1 | 770 | 400 | 550 |
| IV | 9.3 | 8.7 | 11.5 | 375 | 305 | 331 |
| V | 19.3 | 10.4 | 13.9 | 428 | 265 | 328 |

Example 11: Comparison of mAS3opt50 to Complex Medium and Complex Medium Supplemented with Yeast Extract The starting complex medium ("HP") was a soy hydrolysate-based formulation: 28 g/L HYPEP 1510 (Kerry Group Services Ltd.), 3.5 g/L NaCl, 0.7 g/L $KH_2PO_4$, 0.0182 g/L $CaCl_2.2H_2O$, 1 g/L $MgSO_4.7H_2O$, 0.84 g/L $NaHCO_3$, and 80 g/L glucose. A fermentation of six GBS serotypes in this medium gave growth and titers that were substantially lower than in mAS3opt50. Therefore, HP was supplemented with 10 g/L AMBERFERM 5902 (Sensient Technologies Corp.) ("HPYE"), an ultrafiltered yeast extract. The HPYE medium had substantially improved cell density and polysaccharide titers compared to the HP medium. While HPYE showed increased growth in almost all serotypes compared to mAS3opt50, the polysaccharide titers were somewhat less in the HPYE media. All data are shown in Table 21 below.

TABLE 21

Comparison of mAS3opt50 to Complex Medium and Complex Medium Supplemented with Yeast

| GBS Serotype | Growth ($OD_{600}$) | | | Polysaccharide (m9/L) | | |
|---|---|---|---|---|---|---|
| | mAS3opt50 | HP | HPYE | mAS3opt50 | HP | HPYE |
| Ia | 18.6 | 9.8 | 17.9 | 930 | 410 | 770 |
| Ib | 19.3 | 8.1 | 22.7 | 560 | 120 | 460 |
| II | 17.0 | 13.1 | 19.1 | 440 | 150 | 230 |
| III | 13.9 | 11.4 | 19.3 | 750 | 440 | 630 |
| IV | 10.4 | 18.4 | 16.5 | 360 | 120 | 280 |
| V | 18.0 | 11.6 | 20.5 | 390 | 170 | 390 |

Example 12: Titration of Yeast Extract in Complex Medium

A titration was performed to determine the concentration of yeast extract supplementation to confer optimal growth and polysaccharide production. GBS serotype V was used as a model to gauge the effect of yeast extract supplementation with AMBERFERM 5902 (Sensient Technologies Corp.) at 0 g/L, 2.5 g/L, 5 g/L, 10 g/L, 20 g/L and 40 g/L. As shown in Table 22, the data indicated that supplementation with as little as 2.5 g/L yeast was sufficient to stimulate growth and production of capsular polysaccharide. However, the optimum concentration of yeast extract supplementation was 10 g/L because the addition of greater amounts conferred no additional benefit.

TABLE 22

Effect of Yeast Extract Titration on Growth and Polysaccharide Production in Complex Medium

| Yeast extract concentration (g/L) | Growth ($OD_{600}$) | Polysaccharide (mg/L) |
|---|---|---|
| 0 | 10.9 | 64 |
| 2.5 | 18.0 | 259 |
| 5.0 | 19.6 | 291 |
| 10.0 | 20.4 | 320 |
| 20.0 | 20.7 | 282 |
| 40.0 | 23.5 | 279 |

Example 13: Yeast Extract Supplementation of Defined Media

Given the positive impact of supplementation with yeast extract on polysaccharide titer in the complex medium, experiments that examined supplementation of GBS mAS3 with AMBERFERM 5902 (Sensient Technologies Corp.) was performed. GBS mAS3 supplemented with the ultrafiltered yeast extract ("R17YE") was compared to GBS mAS3 and mAS3opt50. Yeast extract supplementation of R17 dramatically improved polysaccharide titer compared to both GBS mAS3 and mAS3opt50 (see Table 23).

TABLE 23

Comparison of Yeast Extract-Supplemented GBS mAS3, GBS mAS3, and mAS3opt50

| GBS Serotype | Growth ($OD_{600}$) | | | Polisaccharide (mg/L) | | |
|---|---|---|---|---|---|---|
| | GBS mAS3 | R17YE | mAS3opt50 | GBS mAS3 | R17YE | mAS3opt50 |
| Ia | 8.9 | 20.0 | 18.6 | 750 | 750 | 930 |
| Ib | 8.3 | 18.8 | 19.3 | 270 | 690 | 560 |
| II | 9.7 | 18.2 | 17.0 | 190 | 350 | 440 |
| III | 5.1 | 16.5 | 13.9 | 270 | 750 | 750 |
| IV | 8.2 | 16.2 | 10.4 | 260 | 560 | 360 |
| V | 9.6 | 18.8 | 18.0 | 220 | 470 | 390 |

A study was then performed to compare supplementation with varying concentrations of ultrafiltered yeast extract to supplementation with varying concentrations of a commercially available "synthetic" yeast extract from BD Biosciences (BD RECHARGE). GBS serotype V was used as a model. The data shown in Table 24 indicates that, although 20 g/L yeast extract (either ultrafiltered or synthetic) confers an improvement in growth, there is no corresponding increase in polysaccharide titer. Supplementation with the synthetic yeast extract improves growth over GBS mAS3 control, but does not confer the maximum titer that is achieved with the ultrafiltered yeast extract.

TABLE 24

Comparison of Varying Concentrations of Ultrafiltered
Yeast Extract and Synthetic Yeast Extract

| GBS mAS3 Supplementation | Growth (OD$_{600}$) | Polysaccharide (mg/L) |
|---|---|---|
| None | 9.8 | 240 |
| 5 g/L AMBERFERM 5902 | 15.5 | 440 |
| 10 g/L AMBERFERM 5902 | 18.1 | 470 |
| 20 g/L AMBERFERM 5902 | 26.2 | 480 |
| 10 g/L BD RECHARGE | 18.0 | 320 |
| 20 g/L BD RECHARGE | 19.2 | 320 |

Example 14: Analysis of Constant Glucose Feed Fermentation

A constant glucose feed was examined for its effect in supporting polysaccharide titers with the mAS3opt50 media using various GBS serotypes as a model. A comparison of batching 50 g/L glucose and glucose-fed fermentations (10 g/L glucose batched and the remaining 40 g/L fed at a constant rate over the course of 7 hours beginning at 3-4 hours of EFT) indicated that comparable growth and polysaccharide titers were achieved across all serotypes (see Table 25). The fermentation control parameters were otherwise those presented in Example 2.

TABLE 25

Glucose Fed-Batch Fermentation with mAS3opt50 Media

| GBS Serotype | Growth OD$_{600}$ | | Polysaccharide (mg/L) | |
|---|---|---|---|---|
| | Batch | Feed | Batch | Feed |
| Ia | 11.0 | 13.5 | 610 | 790 |
| Ib | 15.3 | 17.6 | 530 | 460 |
| II | 15.1 | 14.4 | 270 | 300 |
| III | 11.7 | 13.2 | 590 | 660 |
| IV | 9.7 | 9.3 | 330 | 340 |
| V | 15.2 | 15.0 | 280 | 360 |

Example 15: Glucose Fed-Batch Fermentation with HPYE and GBS mAS3 Media

Fed-batch fermentation was also examined for HPYE and GBS mAS3 media using GBS serotype V as a model. The fermentation was initiated with 10 g/L glucose batched, and then 70 g/L glucose was fed over the course of 5 hours after 3-4 hours of EFT. The fermentation was otherwise formulated as in Example 2. The data presented in Table 26 indicates that the fed-batch approach gives ~ equivalent productivity for GBS mAS3 versus the batch approach. The fed approach supports polysaccharide production in HPYE, but at a somewhat lower productivity than batch.

TABLE 26

Comparison of Growth and Polysaccharide Production
of Serotype V in Batch and Glucose Fed-Batch
in mAS3opt50, HPYE and GBS mAS3 Media

| Basal medium | Growth (OD$_{600}$) | | Polysaccharide (mg/L) | |
|---|---|---|---|---|
| | Batch | Fed | Batch | Fed |
| mAS3opt50 | 15.1 | 15.0 | 280 | 360 |
| HPYE | 19.8 | 23.4 | 390 | 334 |

TABLE 26-continued

Comparison of Growth and Polysaccharide Production
of Serotype V in Batch and Glucose Fed-Batch
in mAS3opt50, HPYE and GBS mAS3 Media

| Basal medium | Growth (OD$_{600}$) | | Polysaccharide (mg/L) | |
|---|---|---|---|---|
| | Batch | Fed | Batch | Fed |
| GBS mAS3 | 9.7 | 10.1 | 175 | 182 |

Example 16: Perfusion Fermentation

Perfusion experiments using the Modified AS3 medium described in Example 1 were performed on 13 serotypes of S. pneumoniae. The medium was inoculated and run in batch mode in a 2 L bioreactor for about 4-10 hours until the OD$_{600}$ reached 3-7. The culture was then circulated through a perfusion system where spent medium and waste products were removed and the culture volume was maintained by the introduction of fresh medium. The perfusion began at an initial rate of 0.13 VVH and gradually ramped to 0.80 VVH over the course of 3-5 hours, at which point the perfusion batch was ended. The data, shown in Table 27 below, indicates a significant increase in biomass levels with a corresponding increase in polysaccharide produced compared to batch fermentation in Example 1.

TABLE 27

S. pneumoniae Growth and Polysaccharide Production in
Perfusion Fermentation Compared to Batch Fermentation

| | Perfusion | | Batch | |
|---|---|---|---|---|
| Serotype | Growth OD600 | Polysaccharide (g/L) | Growth OD600 | Polysaccharide (g/L) |
| 1 | 36 | 3.4 | 9.1 | 1.38 |
| 3 | 20 | 2.4 | 11.5 | 3.19 |
| 4 | 51 | 2.4 | 9.5 | 0.50 |
| 5 | 32 | 2.7 | 7.5 | 0.40 |
| 6A | 42 | 5.3 | 6.6 | 1.10 |
| 6B | 30 | 3.5 | 6.0 | 2.00 |
| 7F | 51 | 5.6 | 8.0 | 0.70 |
| 9V | 37 | 5.1 | 7.4 | 0.54 |
| 14 | 30 | 2.2 | 6.8 | 1.10 |
| 18C | 35.5 | 5.5 | 7.0 | 0.97 |
| 19A | 26 | 4.9 | 5.0 | 2.40 |
| 19F | 55 | 5.4 | 5.5 | 0.86 |
| 23F | 37 | 4.4 | 6.5 | 1.10 |

Example 17: Comparison of Perfusion and Batch Fermentation Methods in Three Different Media Perfusion experiments using GBS mAS3 or HPYE as the basal media were performed. A 1× medium (containing 0.5× glucose) was inoculated and run in batch mode (5 L working volume) for about 3 hours. When the OD approached 1-5 OD, perfusion with 0.5× medium began at an initial rate of 0.13 VVH for approximately one hour. The rate was ramped to 1.20 VVH over the course of 6-7 hours at which point the perfusion batch was ended. The data for GBS mAS3 perfusion, shown in Table 28 below, indicates an approximate 1.4-2 fold increase in cell density over batch mode, with a concomitant increase in polysaccharide titer.

TABLE 28

| GBS Serotype | Growth OD$_{600}$ | | Polysaccharide (mg/L) | |
|---|---|---|---|---|
| | Batch | Perfusion | Batch | Perfusion |
| Ia | 18.6 | 25.6 | 930 | 1300 |
| Ib | 19.3 | 41.6 | 560 | 740 |
| II | 17.0 | 27.7 | 440 | 860 |
| III | 13.9 | 32.3 | 750 | 1770 |
| IV | 8.2 | ND | 260 | ND |
| V | 18.0 | 28.1 | 390 | 730 |

*ND = Test not done.

The data for perfusion based on the HPYE complex medium is shown in Table 29 below. In general, perfusion resulted in a greater than 2-fold increase in cell density over batch and a 2 to 3.5-fold improvement in polysaccharide titer.

TABLE 29

| GBS Serotype | Growth OD$_{600}$ | | Polysaccharide (mg/L) | |
|---|---|---|---|---|
| | Batch | Perfusion | Batch | Perfusion |
| Ia | 17.9 | 50.6 | 770 | 1940 |
| Ib | 22.7 | 27.9 | 460 | 1100 |
| II | 19.1 | 44.0 | 230 | 820 |
| III | 19.3 | 39.7 | 630 | 1150 |
| IV | 16.5 | ND | 280 | ND |
| V | 20.5 | 50.0 | 390 | 680 |

*ND = Test not done.

A perfusion in a mAS3opt50-based medium was similarly performed using serotype IV as a model. The harvest OD600 obtained was 16.7; polysaccharide production was 667 mg/L. By comparison, mAS3opt50 batch fermentation presented in Example 8 gave a cell density of 10.4 and a polysaccharide production value of 360 mg/L, evidencing a ~1.9-fold productivity improvement.

In summary, the perfusion fermentation resulted in about a 2-fold or better polysaccharide productivity increase over batch performance in all three media employed.

Aspects of the Invention

The following clauses describe additional embodiments of the invention:

C1. A polysaccharide-producing bacterial cell culture medium comprising a vegetable hydrolysate, a yeast extract, and a carbon source.

C2. The medium of C1, wherein the vegetable hydrolysate is a soy hydrolysate.

C3. The medium of C2, wherein the soy hydrolysate is selected from the group consisting of HYPEP 1510 (Kerry Group Services Ltd.), HYPEP 4601 (Kerry Group Services Ltd.), HYPEP 5603 (Kerry Group Services Ltd.), HY-SOY (Kerry Group Services Ltd.), AMI-SOY (Kerry Group Services Ltd.), N-Z-SOY (Kerry Group Services Ltd.), N-Z-SOY BL4 (Kerry Group Services Ltd.), N-Z-SOY BL7 (Kerry Group Services Ltd.), SHEFTONE D (Kerry Group Services Ltd.), SE50M, SE50MK, soy peptone, BACTO soytone (Difco Laboratories Inc.), NUTRISOY 2207 (ADM), NUTRISOY (ADM), NUTRISOY flour (ADM), and soybean meal.

C4. The medium of C3, wherein the soy hydrolysate is HYPEP 1510 (Kerry Group Services Ltd.).

C5. The medium of any one of C1-C4, wherein the concentration of the vegetable hydrolysate is between about 5 g/L and about 75 g/L.

C6. The medium of C5, wherein the concentration of the vegetable hydrolysate is between about 10 g/L and about 50 g/L.

C7. The medium of C6, wherein the concentration of the vegetable hydrolysate is about 28 g/L.

C8. The medium of any one of C1-C7, wherein the yeast extract is a yeast autolysate, an ultrafiltered yeast extract, or a synthetic yeast extract.

C9. The medium of C8, wherein the yeast extract is an ultrafiltered yeast extract.

C10. The medium of C9, wherein the ultrafiltered yeast extract is AMBERFERM 5902 (Sensient Technologies Corp.), BD DIFCO (BD Biosciences), HYPEP YE (Kerry Group Services Ltd.), ULTRAPEP YE (Kerry Group Services Ltd.), HY-YEST 412 (Kerry Group Services Ltd.), HY-YEST 441 (Kerry Group Services Ltd.), HY-YEST 444 (Kerry Group Services Ltd.), HY-YEST 455 (Kerry Group Services Ltd.), or HY-YEST 504 (Kerry Group Services Ltd.).

C11. The medium of any one of C1-C10, wherein the concentration of yeast extract is between about 1 g/L to about 50 g/L.

C12. The medium of C11, wherein the concentration of yeast extract is between about 5 g/L to about 25 g/L.

C13. The medium of C12, wherein the concentration of yeast extract is about 10 g/L.

C14. The medium of any one of C1-C13, wherein the carbon source is selected from the group consisting of glucose, dextrose, mannitol, lactose, sucrose, fructose, galactose, raffinose, xylose, and mannose.

C15. The medium of C14, wherein the carbon source is glucose.

C16. The medium of any one of C1-C15, wherein the concentration of the carbon source is between about 25 g/L to about 100 g/L.

C17. The medium of C16, wherein the concentration of the carbon source is between about 50 g/L to about 90 g/L.

C18. The medium of C17, wherein the concentration of the carbon source is about 80 g/L.

C19. The medium of any one of C1-C18, wherein the medium comprises soy hydrolysate, an ultrafiltered yeast extract, and glucose.

C20. The medium of any one of C1-C19, wherein the medium further comprises a phosphate-containing ingredient.

C21. The medium of C20, wherein the phosphate-containing ingredient is $Na_2HPO_4$, $K_2HPO_4$, or $KH_2PO_4$.

C22. The medium of any one of C1-C21, wherein the medium further comprises at least one amino acid, vitamin, nucleoside, or inorganic salt.

C23. A polysaccharide-producing bacterial cell culture medium having a total amino acid concentration greater than about 50 mM.

C24. The medium of C23, wherein the medium comprises a total glycine concentration of between about 1.5 mM and about 60.0 mM.

C25. The medium of C24, wherein the total glycine concentration is between about 5.0 mM and about 15.0 mM.

C26. The medium of C25, wherein the total glycine concentration is about 7.5 mM.

C27. The medium of any one of C23-26, wherein the medium comprises a total arginine concentration of between about 1.0 mM and about 30.0 mM.

C28. The medium of C27, wherein the total arginine concentration is between about 1.0 mM and about 20.0 mM.

C29. The medium of C28, wherein the total arginine concentration is about 4.0 mM.

C30. The medium of any one of C23-C29, wherein the medium comprises a total cysteine concentration of between about 0.1 mM and about 5.0 mM.

C31. The medium of C30, wherein the total cysteine concentration is between about 0.1 mM and about 3.5 mM.

C32. The medium of C31, wherein the total cysteine concentration is about 0.4 mM.

C33. The medium of any one of C23-C32, wherein the medium comprises a total serine concentration of between about 5.0 mM and about 75.0 mM.

C34. The medium of C33, wherein the total serine concentration is between about 5.0 mM and about 15.0 mM.

C35. The medium of C34, wherein the total serine concentration is about 7.5 mM, or about 10 mM.

C36. The medium of any one of C23-C35, wherein the medium comprises a total glutamine concentration of between about 1.0 mM and about 30.0 mM.

C37. The medium of C36, wherein the total glutamine concentration is between about 1.0 mM and about 20.0 mM.

C38. The medium of C37, wherein the total glutamine concentration is about 4.0 mM.

C39. The medium of any one of C23-C38, wherein the medium comprises a total concentration of tyrosine of between about 0.1 mM and about 5.0 mM.

C40. The medium of C39, wherein the total tyrosine concentration is between about 1.0 mM and about 3.5 mM.

C41. The medium of C40, wherein the total tyrosine concentration is about 2.9 mM or about 3.0 mM.

C42. The medium of any one of C23-C41, wherein the medium comprises a total concentration of asparagine of between about 5.0 mM and about 50.0 mM.

C43. The medium of C42, wherein the total asparagine concentration is between about 10.0 mM and about 30.0 mM.

C44. The medium of C43, wherein the total asparagine concentration is about 20.0 mM.

C45. The medium of any one of C23-C41, wherein the medium does not contain asparagine.

C46. The medium of any one of C23-C45, wherein the medium further comprises a potassium salt.

C47. The medium of C46, wherein the potassium salt is potassium chloride or potassium sulfate.

C48. The medium of C46 or C47, wherein the total concentration of potassium salt is between about 0.1 g/L and about 25 g/L.

C49. The medium of C48, wherein the total potassium salt concentration is between about 0.2 g/L and about 1.25 g/L.

C50. The medium of C49, wherein the total potassium salt concentration is about 0.9 g/L.

C51. The medium of any one of C23-050, wherein the medium further comprises a carbon source.

C52. The medium of C51, wherein the carbon sources is selected from the group consisting of glucose, dextrose, mannitol, lactose, sucrose, fructose, galactose, raffinose, xylose, and mannose.

C53. The medium of C52, wherein the carbon sources is glucose.

C54. The medium of any one of C51-053, wherein medium comprises a total concentration of the carbon source of between about 25 g/L and about 100 g/L.

C55. The medium of C54, wherein the total concentration of the carbon source is between about 25 g/L and about 80 g/L.

C56. The medium of C55, wherein the total concentration of the carbon source is about 50 g/L.

C57. The medium of any one of C23-056, wherein the medium further comprises sodium bicarbonate.

C58. The medium of C57, wherein the medium comprises a concentration of sodium bicarbonate of between about 0.1 g/L and about 20 g/L.

C59. The medium of C58, wherein the concentration of sodium bicarbonate is between about 0.5 g/L and about 1.0 g/L.

C60. The medium of C59, wherein the concentration of sodium bicarbonate is about 0.84 g/L.

C61. The medium of any one of C23-C60, wherein the medium further comprises a yeast extract.

C62. The medium of C61, wherein the yeast extract is selected from the group consisting of a yeast autolysate, an ultrafiltered yeast extract, and a synthetic yeast extract.

C63. The medium of C62, wherein the yeast extract is an ultrafiltered yeast extract.

C64. The medium of C63, wherein the ultrafiltered yeast extract is AMBERFERM 5902 (Sensient Technologies Corp.), BD DIFCO (BD Biosciences), HYPEP YE (Kerry Group Services Ltd.), ULTRAPEP YE (Kerry Group Services Ltd.), HY-YEST 412 (Kerry Group Services Ltd.), HY-YEST 441 (Kerry Group Services Ltd.), HY-YEST 444 (Kerry Group Services Ltd.), HY-YEST 455 (Kerry Group Services Ltd.), or HY-YEST 504 (Kerry Group Services Ltd.).

C65. The medium of any one of C61-C64, wherein the concentration of yeast extract is between about 1 g/L to about 50 g/L.

C66. The medium of C65, wherein the concentration of yeast extract is between about 5 g/L to about 25 g/L.

C67. The medium of C66, wherein the concentration of yeast extract is about 10 g/L.

C68. The medium of any one of C23-C67, wherein the medium comprises at least about 50 mM of amino acids, a potassium salt, a carbon source, and optionally, a yeast extract.

C69. The medium of C68, wherein the medium comprises at least about 50 mM of amino acids, between about 5.0 mM and about 15.0 mM of glycine, between about 0.2 g/L and about 1.25 g/L of a potassium salt, between about 25 g/L and about 80 g/L of a carbon source, and between about 5 g/L to about 25 g/L of a yeast extract.

C70. The medium of C69, wherein the medium comprises at least about 60 mM of amino acids, about 7.5 mM of glycine, about 0.9 g/L of potassium chloride, 50 g/L of glucose, and about 10 g/L of an ultrafiltered yeast extract.

C71. A method of cultivating a polysaccharide-producing bacteria comprising a) adding a medium of any one of C1-C70 to a bioreactor, b) seeding the medium with a polysaccharide-producing bacteria, and c) cultivating the bacteria by fermentation, wherein said cultivation comprises the addition of a nutrient at a constant rate to the medium.

C72. The cultivation method of C71, wherein the nutrient is a carbon source.

C73. The cultivation method of C72, wherein the carbon source is glucose.

C74. The cultivation method of any one of C71-C73, wherein the cultivated bacteria have a cell density of at least 9.0.

C75. The cultivation method of any one of C71-C74, wherein the cultivated bacteria have a polysaccharide concentration of at least about 250 mg/L.

C76. The cultivation method of any one of C71-C75, wherein the polysaccharide-producing bacteria is selected from the group consisting of *Streptococcus agalactiae, Streptococcus pneumoniae, Staphylococcus aureus, Neisseria meningitidis, Escherichia coli, Salmonella typhi, Hae-* mophilus influenzae, Klebsiella pneumoniae, Enterococcus faecium, and Enterococcus faecalis.

C77. A method of cultivating a polysaccharide-producing bacteria comprising a) adding a medium of any one of C1-C70 to a bioreactor, b) seeding the medium with a polysaccharide-producing bacteria, and c) cultivating the bacteria by perfusion, wherein the cultivation comprises (i) removing spent medium from the culture, (ii) adding fresh medium, and (iii) retaining the bacteria.

C78. The cultivation method of C77, wherein the rate of perfusion is between about 0.07 VVH to about 2.00 VVH.

C79. The cultivation method of C78, wherein the rate of perfusion is between about 0.67 VVH to about 1.33 VVH.

C80. The cultivation method of C79, wherein the rate of perfusion is about 1.20 VVH.

C81. The cultivation method of C77, wherein the rate of perfusion is varied.

C82. The cultivation method of C81, wherein the perfusion starts at a first rate and the rate is increased to a second rate.

C83. The cultivation method of C81, wherein the perfusion starts at a first rate and the rate is decreased to a second rate.

C84. The cultivation method of any one of C77-C83, wherein the duration of perfusion is between about 1 hour and about 15 hours.

C85. The cultivation method of C84, wherein the duration of perfusion is between about 1 hour and about 10 hours.

C86. The cultivation method of C85, wherein the duration of perfusion is about 7 hours.

C87. The cultivation method of any one of C77-C86, wherein the cell growth of the cultivated bacteria is at least 2-fold greater than the cell growth in a batch fermentation system.

C88. The cultivation method of any one of C77-C87, wherein the cultivated bacteria have reached a cell density of at least 20.0.

C89. The cultivation method of any one of C77-C88, wherein the cultivated bacteria have reached a polysaccharide concentration of at least about 600 mg/L.

C90. The cultivation method of any one of C77-C89, wherein wherein the polysaccharide-producing bacteria is selected from the group consisting of *Streptococcus agalactiae, Streptococcus pneumoniae, Staphylococcus aureus, Neisseria meningitidis, Escherichia coli, Salmonella typhi, Haemophilus influenzae, Klebsiella pneumoniae, Enterococcus faecium*, and *Enterococcus faecalis*.

The invention claimed is:

1. A method of cultivating a polysaccharide-producing bacteria selected from *Streptococcus pneumoniae* and *Streptococcus agalactiae*, comprising:
   (a) adding a defined medium to a bioreactor, wherein said defined medium comprises
      (i) a total amino acid concentration of at least 60 mM;
      (ii) a total glycine concentration of between 1.5 mM and 60.0 mM;
      (iii) a total potassium chloride concentration of between 0.31 g/L and 24.31 g/L; and
      (iv) a carbon source;
   (b) seeding the defined medium with the polysaccharide-producing bacteria; and
   (c) cultivating the bacteria by fermentation, wherein a nutrient is added during the cultivating step.

2. The method of claim 1, wherein the carbon source is glucose.

3. The method of claim 1, wherein the concentration of the carbon source is between about 50 g/L to about 90 g/L.

4. The method of claim 3, wherein the concentration of the carbon source is about 80 g/L.

5. The method of claim 1, wherein the cultivated bacteria have a polysaccharide concentration of at least about 250 mg/L.

6. The method of claim 1, wherein the cultivated bacteria have a cell density of at least 9.0.

\* \* \* \* \*